(12) United States Patent
Okajima et al.

(10) Patent No.: US 12,324,711 B2
(45) Date of Patent: Jun. 10, 2025

(54) DATA ANALYTICS AND INTERFACE PLATFORM FOR PORTABLE SURGICAL ENCLOSURE

(71) Applicant: SURGIBOX INC., Brookline, MA (US)

(72) Inventors: Stephen Michael Okajima, Brookline, MA (US); Mike Horia Mihail Teodorescu, Brookline, MA (US); Debbie Lin Teodorescu, Brookline, MA (US); Oded Biran, Brookline, MA (US)

(73) Assignee: SurgiBox Inc., Cambridge, MA (US)

( * ) Notice: Subject to any disclaimer, the term of this patent is extended or adjusted under 35 U.S.C. 154(b) by 1117 days.

(21) Appl. No.: 17/276,622

(22) PCT Filed: Sep. 17, 2019

(86) PCT No.: PCT/US2019/051502
§ 371 (c)(1),
(2) Date: Mar. 16, 2021

(87) PCT Pub. No.: WO2020/061037
PCT Pub. Date: Mar. 26, 2020

(65) Prior Publication Data
US 2022/0039908 A1 Feb. 10, 2022

Related U.S. Application Data

(60) Provisional application No. 62/732,480, filed on Sep. 17, 2018.

(51) Int. Cl.
*A61B 90/40* (2016.01)
*A61B 5/0205* (2006.01)
(Continued)

(52) U.S. Cl.
CPC ............ *A61B 90/40* (2016.02); *A61B 5/0205* (2013.01); *A61B 34/30* (2016.02); *A61B 46/27* (2016.02);
(Continued)

(58) Field of Classification Search
CPC ...... A61G 10/00; A61G 10/005; A61G 10/02; A61B 34/30; A61B 34/32; A61B 34/35;
(Continued)

(56) References Cited

U.S. PATENT DOCUMENTS

| | | | |
|---|---|---|---|
| 3,051,164 A | 8/1959 | Trexler | |
| 3,692,024 A | 9/1972 | Von Otto | |

(Continued)

FOREIGN PATENT DOCUMENTS

| | | | |
|---|---|---|---|
| CN | 204274654 U | 4/2015 | |
| CN | 204394702 U | 6/2015 | |

(Continued)

OTHER PUBLICATIONS

International Search Report and Written Opinion in PCT/US/2021/058496 issued Feb. 8, 2022.

(Continued)

*Primary Examiner* — Carrie R Dorna
(74) *Attorney, Agent, or Firm* — Fish & Richardson P.C.

(57) ABSTRACT

Provided herein is a portable surgical system designed for interoperability with surgical or research tools and processes. The portable surgical system may comprise a portable enclosure and one or more sensors. Also provided herein are methods for training surgery robots for use with the system and manufacturing the portable surgical system.

20 Claims, 15 Drawing Sheets

(51) Int. Cl.
  *A61B 34/30*  (2016.01)
  *A61B 46/27*  (2016.01)
  *A61B 46/20*  (2016.01)

(52) U.S. Cl.
  CPC ... *A61B 2046/205* (2016.02); *A61B 2090/401* (2016.02); *A61B 2562/0219* (2013.01); *A61B 2562/0247* (2013.01); *A61B 2562/0271* (2013.01)

(58) Field of Classification Search
  CPC ...... A61B 34/37; A61B 2034/301–306; A61B 90/40; A61B 2090/401
  See application file for complete search history.

(56) References Cited

U.S. PATENT DOCUMENTS

| | | | |
|---|---|---|---|
| 3,850,172 | A | 11/1974 | Cazalis et al. |
| 4,275,719 | A | 6/1981 | Mayer |
| 4,367,728 | A | 1/1983 | Mutke |
| 4,865,049 | A | 9/1989 | Gatti |
| 4,950,222 | A | 8/1990 | Scott et al. |
| 5,083,558 | A | 1/1992 | Thomas et al. |
| 5,170,804 | A | 12/1992 | Glassman |
| 5,299,582 | A | 4/1994 | Potts |
| 5,728,041 | A | 3/1998 | Fowler, Jr. |
| 5,979,450 | A | 11/1999 | Baker et al. |
| 6,001,057 | A | 12/1999 | Bongiovanni et al. |
| 6,199,551 | B1 | 3/2001 | Kuslich |
| 6,321,764 | B1 | 11/2001 | Gauger et al. |
| 10,016,252 | B1* | 7/2018 | Wren, Sr. .............. A61G 10/005 |
| 2002/0045796 | A1 | 4/2002 | O'Connor et al. |
| 2002/0112754 | A1 | 8/2002 | Gauger et al. |
| 2003/0060831 | A1 | 3/2003 | Bonutti |
| 2007/0102005 | A1 | 5/2007 | Bonutti |
| 2008/0041399 | A1 | 2/2008 | Kriek |
| 2008/0047567 | A1 | 2/2008 | Bonutti |
| 2009/0124987 | A1 | 5/2009 | Eriksson et al. |
| 2009/0216069 | A1 | 8/2009 | Woodcock et al. |
| 2010/0234794 | A1 | 9/2010 | Weadock et al. |
| 2011/0118748 | A1 | 5/2011 | Itkowitz |
| 2011/0301459 | A1 | 12/2011 | Gharib |
| 2012/0267499 | A1* | 10/2012 | Abri ....................... A61B 90/37 312/294 |
| 2016/0008081 | A1 | 1/2016 | Forsell |
| 2016/0074268 | A1 | 3/2016 | Breegi et al. |
| 2016/0166455 | A1 | 6/2016 | Steinert |
| 2016/0331461 | A1 | 11/2016 | Cheatham, III et al. |
| 2017/0128769 | A1* | 5/2017 | Long ..................... A61G 10/02 |
| 2017/0340407 | A1 | 11/2017 | Ahrens |
| 2018/0085559 | A1 | 3/2018 | Laby et al. |
| 2018/0250075 | A1 | 9/2018 | Cho |
| 2021/0290337 | A1 | 9/2021 | Teodorescu et al. |
| 2024/0156566 | A1 | 5/2024 | Teodorescu |

FOREIGN PATENT DOCUMENTS

| | | |
|---|---|---|
| CN | 204394708 U | 6/2015 |
| CN | 104768493 A | 7/2015 |
| CN | 105877846 A | 8/2016 |
| CN | 107428909 A | 12/2017 |
| CN | 107635505 A | 1/2018 |
| CN | 111655111 A | 9/2020 |
| GB | 1604033 A | 12/1981 |
| JP | H06-70725 U | 10/1994 |
| WO | WO 1986/06272 A1 | 11/1986 |
| WO | WO 1991/07921 A1 | 6/1991 |
| WO | WO 1993/016741 A1 | 9/1993 |
| WO | WO 2005/092229 A1 | 10/2005 |
| WO | WO 2011/041665 A2 | 4/2011 |
| WO | WO 2013/012367 A1 | 1/2013 |
| WO | WO-2014109706 A1 | 7/2014 |
| WO | WO 2014/145032 A1 | 9/2014 |
| WO | WO 2014/189874 A1 | 11/2014 |
| WO | WO 2016/102018 A1 | 6/2016 |
| WO | WO-2018014003 A1 | 1/2018 |
| WO | WO-2018144809 A1 | 8/2018 |
| WO | WO-2020061037 A1 | 3/2020 |
| WO | WO 2020/227706 A1 | 11/2020 |
| WO | WO 2022/182394 A1 | 9/2022 |

OTHER PUBLICATIONS

Chinese Patent Application No. 20198007545465 First Office Action dated Jan. 11, 2024.
Miller, Sally A., Designof an Ultraportable Surgical Enclosure for Low Resource Environments, Massachusetts Institute of Technology, Feb. 2018 [retrieved on Oct. 24, 2019], Retrieved from internet:< url: https://pdfs.semanticscholar.org/2105/5a4e21700bc04c8209f48bcfbadf6d1Occ47.pdf</url:>.
Allegranzi et al., "Burden of endemic health-care-associated infection in developing countries: systematic review and meta-analysis," The Lancet, Jan. 15, 2011, 377(9761):228-41.
American Society of Heating, Refrigerating and Air-Conditioning Engineers, "2011 ASHRAE Handbook—HVAC Applications: Heating Ventilation and Air Conditioning Applications," Jun. 15, 2011, 1104 pages.
ashrae.org, "Ventilation of Health Care Facilities 170-2013," Feb. 2014, retrieved Sep. 28, 2022 from URL <https://permissions.iengineering.com/Content/pdf>, 28 pages.
AU Office Action in Australian Application No. 2017297605, dated Dec. 24, 2021, 3 pages.
AU Office Action in Australian Appln. No. 2017297605, dated May 20, 2022, 4 pages.
AU Office Action in Australian Appln. No. 2017297605, dated Oct. 13, 2022, 6 pages.
CA Office Action in Canadian Appln. No. 3,030,844, dated Apr. 13, 2022, 4 pages.
CN Office Action in Chinese Appln. No. 201780055697.4, dated May 8, 2021, 16 pages.
CN Office Action in Chinese Appln. No. 201980075456.5, mailed on Jan. 21, 2025, 25 pages (with English translation).
CN Office Action in Chinese Appln. No. 201980075456.5, mailed on Sep. 9, 2024, 26 pages (with English translation).
CN Office Action in Chinese Appln. No. 202210145091.2, mailed on Mar. 27, 2024, 19 pages (with English translation).
Edmiston et al., "Molecular epidemiology of microbial contamination in the operating room environment: Is there a risk for infection?," Surgery, Oct. 1, 2005, 138(4):573-82.
EP Communication in European Appln. No. 17828590.4, dated May 12, 2020, 7 pages.
EP Extended European Search Report in European Appln. No. 1782590.4, dated Jun. 28, 2019, 9 pages.
EP Extended Search Report in European Appln. No. 21216566.6, dated May 16, 2022, 9 pages.
EP Notice of Opposition in European Appln. No. 17828590.4, dated Sep. 28, 2022, 30 pages.
EP Office Action in European Appln. No. 19861892.8, mailed on Mar. 12, 2025, 5 pages.
EP Supplementary European Search Report in European Appln. No. 19861892.8, mailed on May 31, 2022, 7 pages.
IL Office Action in Israeli Appln. No. 2627195, dated Jul. 27, 2022, 10 pages (with English translation).
IL Office Action in Israeli Appln. No. 264163, dated Dec. 27, 2021, 12 pages (with English translation).
Kilinc, "A review of isolation gowns in healthcare: fabric and gown properties," Journal of Engineered Fibers and Fabrics, Sep. 2015, 10(3), 11 pages.
KR Office Action in Korean Appln. No. 7004609, dated Jan. 19, 2022, 10 pages (with English translation).
Kunze, "Mobiler Laminar Flow—eine neue Technologie fur den OP-Saal," Medizintechnik, Jan. 2008, 128(6):213, 36 pages (with English translation).
PCT International Preliminary Report on Patentability in International Appln. No. PCT/US2017/042266, dated Jan. 15, 2019, 9 pages.

(56) References Cited

OTHER PUBLICATIONS

PCT International Preliminary Report on Patentability in International Appln. No. PCT/US2019/051502, mailed on Mar. 9, 2021, 7 pages.

PCT International Preliminary Report on Patentability in International Appln. No. PCT/US2022/020041, mailed on Sep. 12, 2023, 14 pages.

PCT International Search Report and Written Opinion in International Appln. No. PCT/US2019/051502, mailed on Nov. 19, 2019, 9 pages.

PCT International Search Report and Written Opinion in International Appln. No. PCT/US2022/020041, mailed on Mar. 11, 2022, 22 pages.

PCT International Search Report/Written Opinion in International Appln. No. PCT/US2017/042266, dated Sep. 28, 2017, 9 pages.

Sehulster et al., "Guidelines for Environmental Infection Control in Health-Care," May 27, 2003, retrieved Nov. 1, 2021 from URL: <https://www.cdc.gov/mmwr/preview/mmwrhtml/rr5210a1.htm>, 60 pages.

Spagnolo et al., "Operating theatre quality and prevention of surgical site infections," Journal of Preventive Medicine and Hygiene, Sep. 2013, 54(3):131, 7 pages.

Teodorescu et al., "An Ultraportable Device Platform for Aseptic Surgery in Field Settings," Journal of Medical Devices, Jun. 1, 2016, 10(2), 2 pages.

Teodorescu et al., "SurgiBox: An ultraportable system to improve surgical safety for patients and providers in austere settings," 2017 IEEE Global Humanitarian Technology Conference (GHTC), Oct. 19, 2017, 5 pages.

TH Office Action in Thai Appln. No. 1901000182, dated Nov. 16, 2020, 4 pages (with English translation).

Whyte et al., "The importance of airborne bacterial contamination of wounds," Journal of Hospital Infection, Jun. 1, 1982, 3(2):123-35.

\* cited by examiner

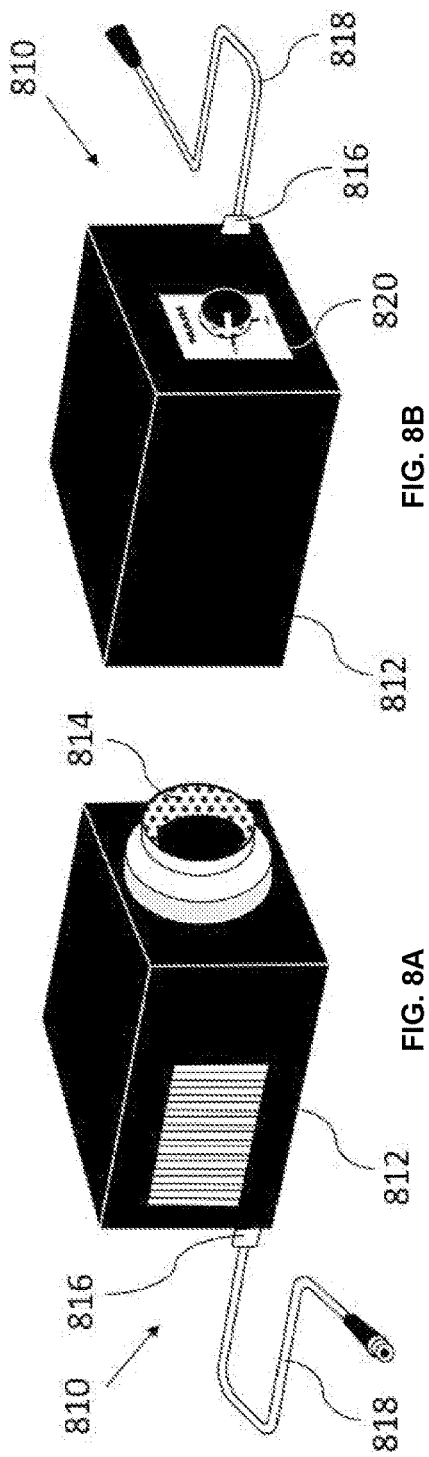
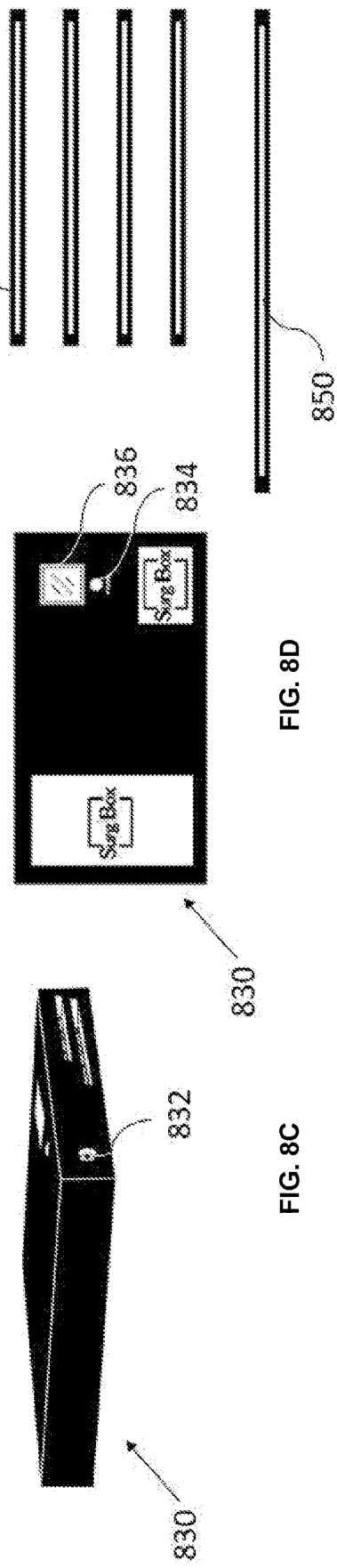
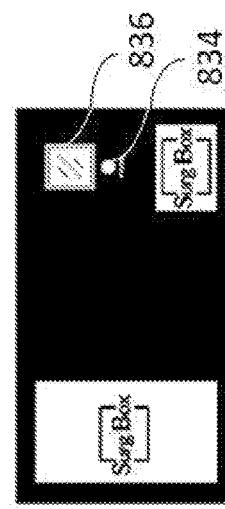
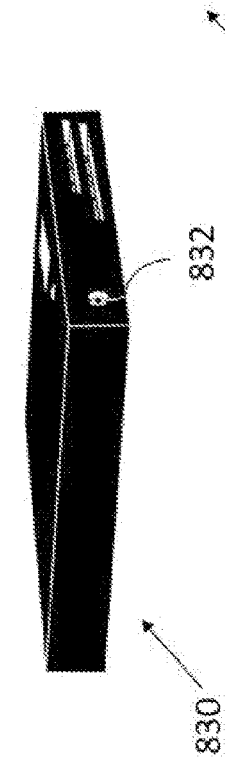

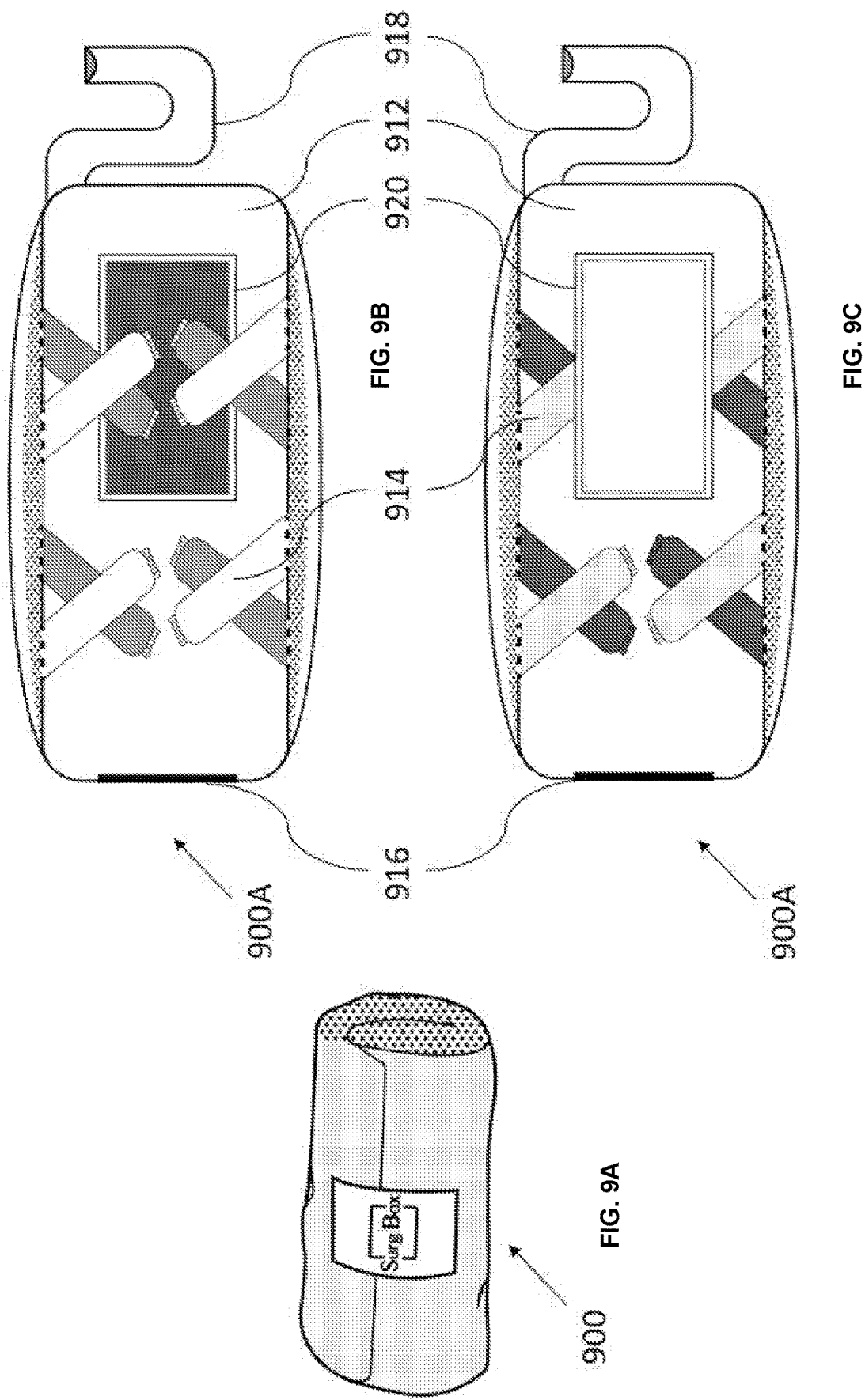

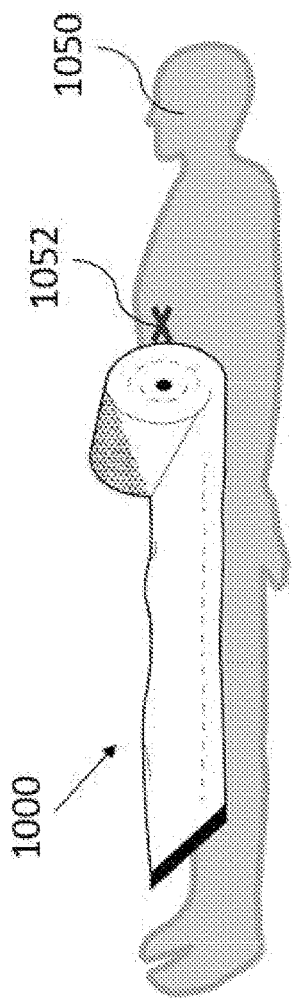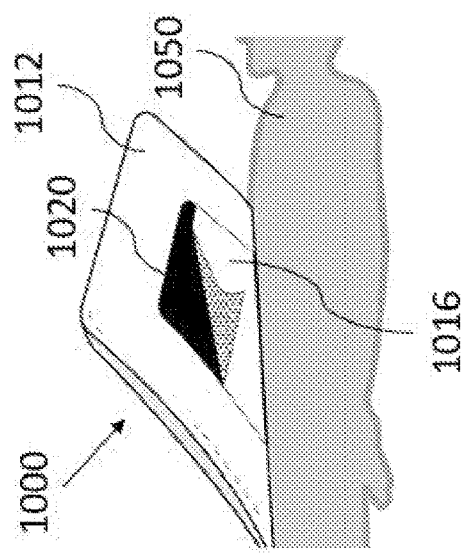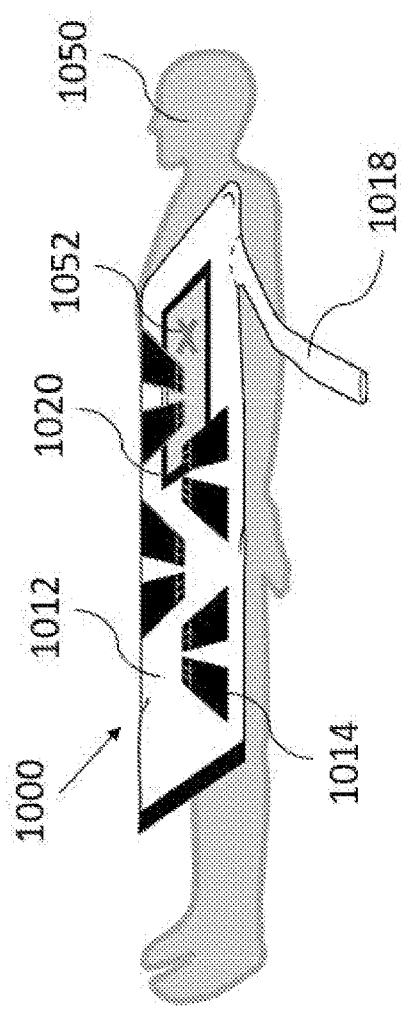
FIG. 10A
FIG. 10B
FIG. 10C

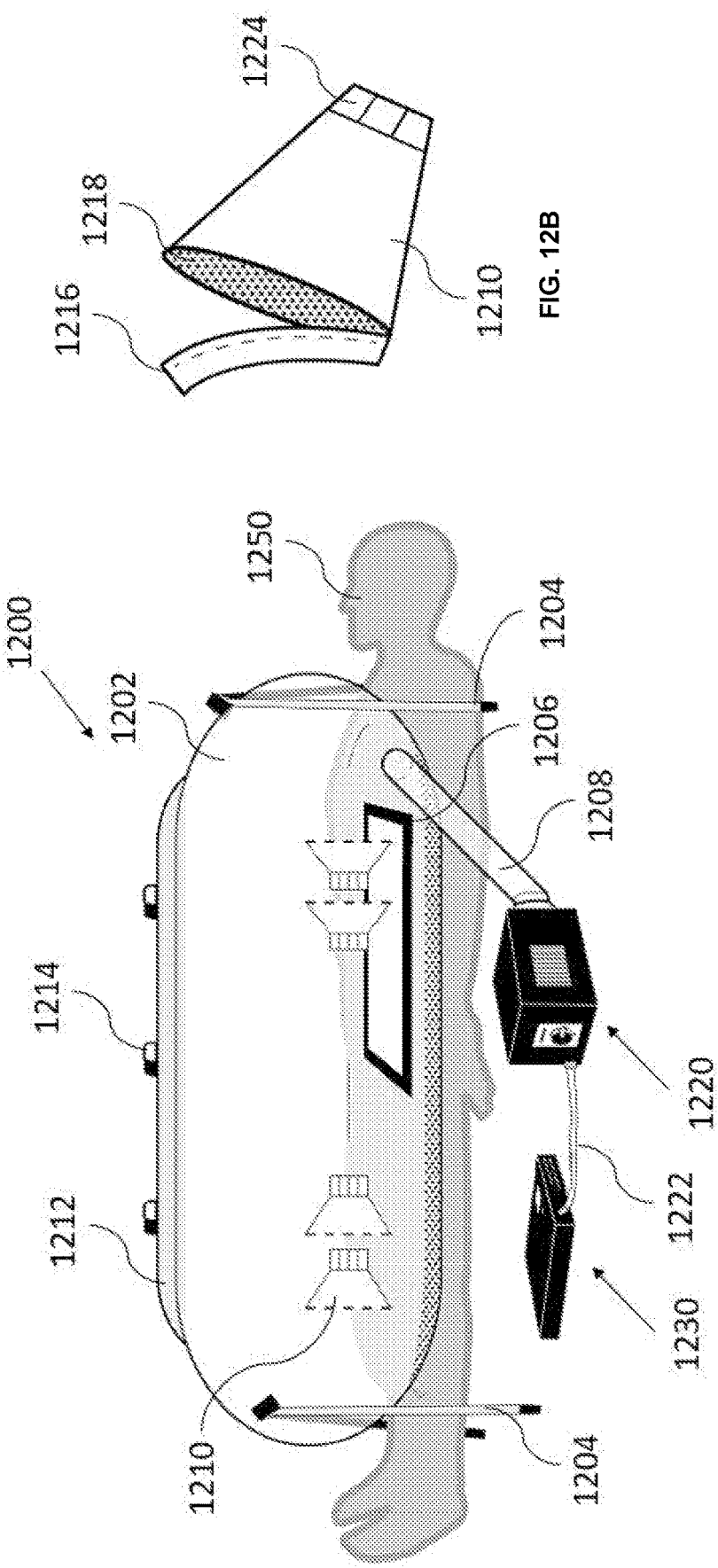

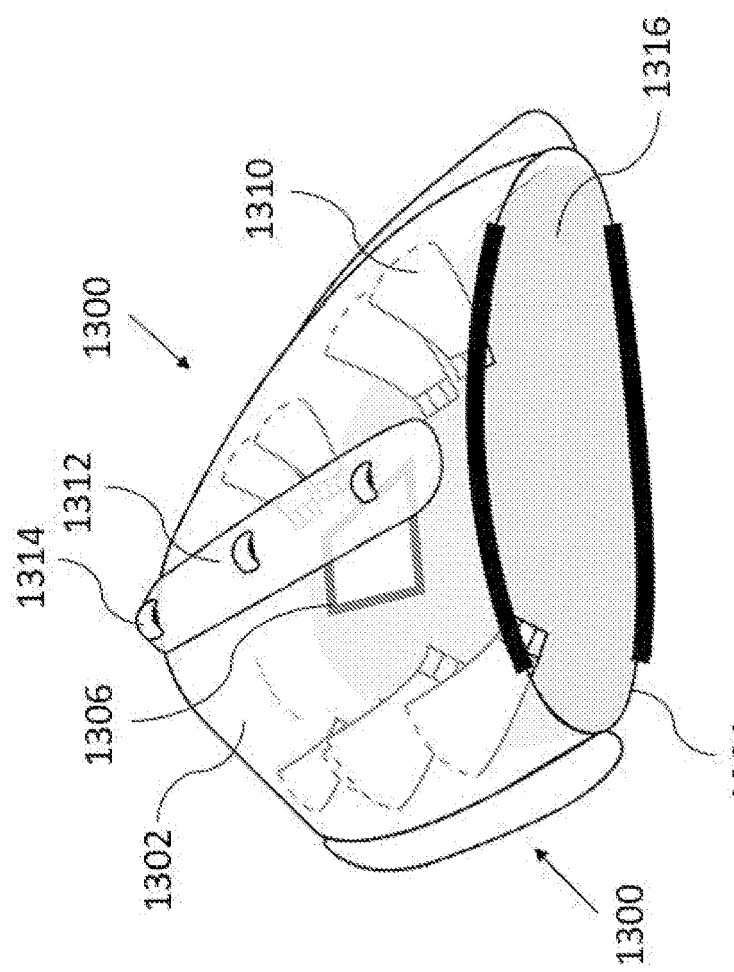
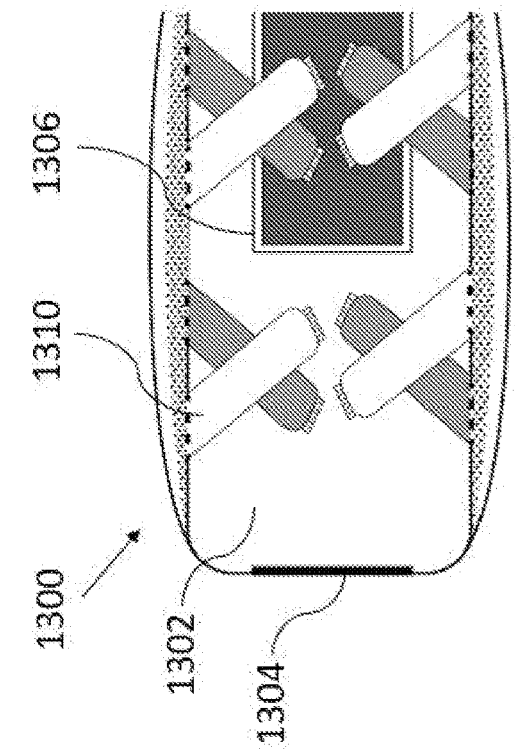
FIG. 13B
FIG. 13A

DATA ANALYTICS AND INTERFACE PLATFORM FOR PORTABLE SURGICAL ENCLOSURE

CROSS-REFERENCE

This application claims priority to U.S. Provisional Patent Application No. 62/732,480, filed Sep. 17, 2018, which is entirely incorporated herein by reference for all purposes.

BACKGROUND

Surgical drapes are used during surgical procedures to create and maintain a sterile environment around the surgical site on the patient to be operated on. The surgical drape creates and maintains a barrier between the sterile environment and the outside non-sterile environment to prevent the passage of microorganisms between the two environments. In particular, the surgical drape prevents the non-sterile environment from contaminating the sterile field, including, for example, the incision and the patient's skin surrounding the incision. Surgical drapes may have an incision opening known as a fenestration through which the surgical procedure can be performed.

SUMMARY

Provided herein are portable surgical systems for regulating intra-operative environments over surgical sites and methods of implementing and using the same. A portable surgical system may address both challenges of patient and provider intraoperative exposure to infectious risks by implementing an ultraportable, self-contained, passive and active, bilateral barrier against exchange of contaminants between incisions and the greater surgical area. A portable surgical system may also provide a platform to train and use surgical robots, which can minimize complications such as surgical site infection; decrease pain and blood loss; speed up recovery; and leave smaller and less noticeable scars. A portable surgical system may include sensors and/or monitors to monitor the vital signs of the patient and to monitor the environment surrounding the patient.

In an aspect, a portable surgical system designed for interoperability with surgical or research tools and processes may comprise: a portable enclosure separating a surgical environment inside the portable enclosure from a user environment outside the portable enclosure, the portable enclosure comprising a flow tube attached to the inside of the portable enclosure and connected to an environmental control system, wherein the flow tube is configured to provide an essentially uniform laminar airflow inside at least part of the portable enclosure; and one or more sensors that comprise at least one motion sensor configured to detect a movement of a surgical instrument, an array of positioning sensors, a medical professional, a patient, a camera or an array of cameras and/or other sensors, a data storage and/or processing system, an object recognition system, a computer interface, a surgical robot, or any combination thereof.

In another aspect, a portable surgical system designed for interoperability with surgical or research tools and processes may comprise: a portable enclosure separating a surgical environment inside the portable enclosure from a user environment outside the portable enclosure, the portable enclosure comprising a flow tube attached to the inside of the portable enclosure and connected to an environmental control system, wherein the flow tube is configured to provide an essentially uniform laminar airflow inside at least part of the portable enclosure; and one or more sensors that comprise at least one sensor configured to detect situational or environmental parameters comprising patient vitals and diagnostics, humidity, temperature, pressure, brightness, and other parameters pertinent to efficacy of the portable surgical system.

In another aspect, a portable surgical system designed for interoperability with surgical or research tools and processes may comprise: a portable enclosure comprising one or more ports allowing for entry, exit, and insertion of surgical and research tools between a surgical environment and a user environment for interoperable use with the portable surgical system, surgical procedure, surgical personnel, patient, or any combination thereof; and one or more sensors that comprise at least one position and motion sensor configured to detect a movement of a surgical instrument, a medical professional, a patient, a surgical robot, or any combination thereof.

In another aspect, a portable surgical system designed for interoperability with surgical or research tools and processes may comprise: a portable enclosure comprising one or more ports allowing for entry, exit, and insertion of surgical and research tools between a surgical environment and a user environment for interoperable use with the portable surgical system, surgical procedure, surgical personnel, patient, or any combination thereof and one or more sensors that comprise at least one sensor configured to detect situational or environmental parameters comprising patient vitals and diagnostics, humidity, temperature, pressure, brightness, and other parameters pertinent to efficacy of the portable surgical system.

In some embodiments, the portable surgical system may further comprise a processor or an information processing system configured to process data collected from the one or more sensors. In some embodiments, the portable enclosure may comprise features for user entry and to enable manipulation of the surgical environment within the portable enclosure. In some embodiments, the portable enclosure may comprise features for fluid retention away from a surgical site.

In some embodiments, the portable enclosure may comprise features for attachment or securing the portable enclosure to the patient. In some embodiments, the portable enclosure may comprise features for allowing a direct incision to be performed through the boundaries of the portable enclosure and a patient's body simultaneously. In some embodiments, the portable enclosure may further comprise a portable device providing power and sterile or substantially clean airflow for the portable enclosure. In some embodiments, the portable enclosure may be flexible with high optical clarity. In some embodiments, the environmental control system may be configured to control the supply of air to the flow tube and to provide sterile or substantially clean conditions inside the portable enclosure.

In some embodiments, the flow tube may be disposed above a surgical site of a patient's body. In some embodiments, the flow tube may be flexible. In some embodiments, the flow tube may be a collapsible tube configured to maintain an open state while airflow through the collapsible tube exerts radial outward pressure sufficient to overcome radial inward pressure of the portable enclosure, and to maintain a closed state when the airflow through the collapsible tube is low such that pressure exerted by the airflow is less than the radial inward pressure of the portable enclosure. In some embodiments, the open or closed state of the collapsible tube may serve as an indicator of airflow status of the portable enclosure.

In some embodiments, the one or more sensors may comprise at least one environmental sensor to detect one or more surgical environment parameters. In some embodiments, the one or more surgical environmental parameters may comprise temperature, pressure, humidity, luminance, heart rate, breathing rate, blood pressure, blood oxygen saturation, electrocardiography, electromyography, skin conductance, airflow, air quality, internal and external gas composition, a chemical composition of the surgical environment, particulate count and composition, $CO_2$ concentration, or any combination thereof. In some embodiments, the at least one motion sensor may comprise an infrared sensor, optical sensor, microwave sensor, ultrasonic sensor, radio-frequency sensors, magnetic sensor, vibration sensor, acceleration sensor, gyroscopic sensor, tilt sensor, piezoelectric sensor, pressure sensor, strain sensor, flex sensor, electromyographic sensor, electrocardiographic sensor, electroencephalographic sensor, thermal sensor, capacitive touch sensor, resistive touch sensor, proximity sensor, infrared sensor, infrared camera, Terahertz camera, position sensor, visible light sensor, visible light camera, or any combination thereof.

In some embodiments, the processor or information procession system may be configured to provide instructions to a surgery robot, provide instructions or alerts to users of the portable enclosure, provide instructions for devices that are designed to be used with the portable enclosure or standard surgical procedures, collect data for use in robotic control, collect data for use in research, collect data for use in quality control and improvement, or any combination thereof. In some embodiments, the instructions may comprise information related to a surgical procedure. In some embodiments, the information related to a surgical procedure may be stored to be transferred with the patient operated on with the intention to maintain continuity of care. In some embodiments, the portable surgical system may further comprise an information storage unit comprising handwriting, phonographic recording, magnetic tape, optical disk, floppy disk, semiconductor storage, floating-gate transistor storage, punched card, paper tape, DNA, RNA, or any combination thereof.

In some embodiments, the portable surgical system may further comprise a physical transfer unit configured to transfer information between operators. In some embodiments, the portable surgical system may further comprise a wireless transfer unit configured to transfer information via frequencies of ELF, SLF, ULF, VLF, LF, MF, HF, VHF, UHF, SHF, EHF, THF, any frequency bands of radio communication for commercial use, light, ultrasounds, or any combination thereof. In some embodiments, the portable surgical system may further comprise a physical information unit separate from a data collection device, wherein the physical information unit is programmed by the data collection device through direct or wireless connection. In some embodiments, the physical information unit may be paired with the patient during transfer to a different healthcare provider through a wristband, dog tag, programmable implant, or other relevant physical medium.

In some embodiments, the portable surgical system may further comprise: a drape; one or more ports; one or more outlets for exhaust; one or more wire tubes; one or more supportive structures; one or more magnifying lenses; one or more suction components; one or more light sources; or any combination thereof.

In some embodiments, the portable surgical system may comprise the one or more outlets for exhaust, wherein the one or more outlets for exhaust are configured to allow for release of and changing of air contained within the portable enclosure. In some embodiments, an outlet for exhaust of the one or more outlets for exhaust may be: a perforation between the user environment and the surgical environment; covered by a filter or porous material; covered by a pressure-sensitive valve; covered by a one-way valve; or any combination thereof.

In some embodiments, the portable surgical system may comprise the drape, wherein the drape is configured to be disposed on or around a surgical site of a patient's body. In some embodiments, the drape may be configured to expose the surgical site. In some embodiments, the portable surgical system may comprise the one or more supportive structures, wherein the one or more supportive structures are configured to maintain a usable volume within the portable enclosure. In some embodiments, the portable surgical system may comprise the one or more supportive structures, wherein the one or more supportive structures may be: created with spring steel; built into the portable enclosure's borders and seams; created with rigid poles or rods that are collapsible or foldable; inflatable; inflatable systems that share pressure inside the portable enclosure; or any combination thereof.

In some embodiments, the portable surgical system may comprise the one or more ports, wherein the one or more ports are configured to enable a user to access the surgical environment without substantially changing volume or pressure of the portable enclosure. In some embodiments, the portable surgical system may comprise the one or more ports, wherein the one or more ports are configured to enable a user to place an extremity within the surgical environment through a port that is designed to stretch over the extremity and hermetically seal at the point of entry over the extremity being inserted.

In some embodiments, the portable surgical system may comprise the one or more ports, wherein a port of the one or more ports are configured to: be perforated so that a user is able to open and configure a size of the port to a desired size; have a removable port cover such that the port is able to be opened; have a drawstring or adjustable diameter so that the size of the port can be changed to a desired size; or any combination thereof. In some embodiments, the portable surgical system may comprise the one or more ports, wherein the one or more ports comprise a magnetic strip, a hook-and-loop fastener, a plastic zipper, a flexible inflatable tube, a flexible plastic sheath, a helically wound braid, or any combination thereof.

In some embodiments, the one or more ports may comprise the magnetic strip, wherein the magnetic strip is surrounded by an inflatable material that shares positive pressure within the portable enclosure, inflating around the magnetic strip so that any gaps are filled by the inflated material. In some embodiments, the one or more ports may comprise the magnetic strip, wherein the magnetic strip facilitates closure of the port, wherein an inflatable material is brought closer together by the magnetic strip, thereby creating a two-layered seal between both the magnetic strip and inflated compartments.

In some embodiments, the one or more ports may comprise the flexible inflatable tube, wherein the flexible inflatable tube remains inflated separately from pressure generated inside the portable enclosure. In some embodiments, the port may comprise flexible inflatable tubes becomes inflated as the pressure within the portable enclosure increases. In some embodiments, the one or more ports may comprise the flexible plastic sheath, wherein the flexible plastic sheath extends on both sides of the portable enclosure, and wherein the flexible plastic sheath is created by sealing two layers of material together along two opposing edges, effectively creating a channel to insert devices that are sealed by pressure gradient between the user environment and inside the portable enclosure. In some embodiments, the one or more ports may comprise the helically wound braid, wherein the one or more ports are made of a material that allows for constriction of the one or more ports' circumference when a length of the braid is stretched and elongated.

In some embodiments, the portable surgical system may comprise the one or more ports that comprise magnetic strips surrounded by flexible inflatable tubes. In some embodiments, the magnetic strips may be at least partially sealed when airflow goes through the flexible inflatable tubes.

In some embodiments, the portable surgical system may comprise the one or more outlets for exhaust, wherein the one or more outlets for exhaust comprise at least one one-way pressure sensitive valve. In some embodiments, the at least one one-way pressure sensitive valve may comprise a membrane component and a frame component, wherein the membrane component is part of the portable enclosure, wherein the frame component comprises a sharp edge, and wherein the membrane component is cut by the sharp edge when the frame component is clicked into place. In some embodiments, the frame component may exist as two parts that are designed to snap together on opposing sides of the membrane component. In some embodiments, the membrane component may be cut prior to setting the one-way pressure sensitive valve. In some embodiments, the membrane component may be part of the portable enclosure to be pressurized and may be prepared such that the membrane component requires only the frame component to be functional. In some embodiments, the membrane component may be clamped in either variable tension or variable clamping distances with the intention to modulate the pressure at which the at least one one-way pressure sensitive valve produces exhaust from the portable enclosure. In some embodiments, the at least one one-way pressure sensitive valve may be covered by a removable film or covering that is to be removed after setup of the portable enclosure, ensuring that no accidental backwards flow enters the portable enclosure before the at least one one-way pressure sensitive valve is properly established. In some embodiments, the at least one one-way pressure sensitive valve may release airflow from the surgical environment to the user environment when pressure of the surgical environment is sufficiently greater than the user environment.

In some embodiments, the portable surgical system may comprise the one or more wire tubes, wherein the one or more wire tubes are configured to hold one or more wires, cords, or cables. In some embodiments, the portable surgical system may comprise the one or more wire tubes, wherein a wire tube of the one or more wire tubes is a collapsible tube configured to maintain a collapsed state when airflow through the collapsible tube is low such that pressure exerted by airflow is less than the radial inward pressure of the portable enclosure.

In some embodiments, the portable surgical system may comprise the one or more magnifying glasses, wherein the one or more magnifying glasses are built-in magnifying glasses. In some embodiments, the portable surgical system may comprise the one or more suction components, wherein the one or more suction components are formed of absorbent material.

In some embodiments, the portable surgical system may further comprise a device capable of providing power and clean airflow necessary for maintaining proper function of the portable enclosure and its interoperability with other surgical or research functions. In some embodiments, the clean airflow may be provided by a mechanical filtration, wherein the mechanical filtration comprises a fiberglass filter, a polyester filter, a High Efficiency Particulate Air (HEPA) filter, a Ultra-Low Penetration Air (ULPA) filter, a carbon filter, a ceramic filter, a demister, sedimentation chamber, cyclone separator, rotating scrubber, venturi scrubber, spray chamber, or any combination thereof. In some embodiments, the clean airflow may be provided by a mechanical filtration, wherein the mechanical filtration comprises an electrical filtration method is used to provide clean airflow to the portable enclosure, comprising an ionic filter, UV filter, radiation filter, heat-treated filter, dry electro filter, wet electro filter, or any combination thereof. In some embodiments, the clean airflow may be provided by a combination of mechanical and electrical filtration methods.

In some embodiments, the power may be supplied by an onboard power source comprising a disposable battery, a rechargeable battery, a solar-powered source, a wind-powered source, a hydraulically powered source, a combustion powered source, an electrochemically powered source, a radioactively powered source, or any combination thereof. In some embodiments, the power may be supplied by an external source comprising a one-time use battery, a rechargeable battery, power from an established electrical grid, or any combination thereof.

In some embodiments, a sensor of the one or more sensors is placed inside the portable enclosure. In some embodiments, a sensor of the one or more sensors is placed outside the portable enclosure. In some embodiments, a sensor of the one or more sensors is embedded in a wall of the portable enclosure. In some embodiments, the one or more sensors further comprises a video camera for 3-dimentional vision. In some embodiments, the video camera for 3-dimentional vision is a time of flight camera. In some embodiments, the portable surgical system further comprises: (c) a human operator interface, comprising at least a display and a command console, wherein the display is configured to display information according to commands received from the command console.

In some embodiments, the display comprises a semi-transparent film. In some embodiments, the display is inside the portable enclosure, outside the portable enclosure, or embedded in a wall of the portable enclosure. In some embodiments, the command console is inside the portable enclosure, outside the portable enclosure, or embedded in a wall of the portable enclosure.

In some embodiments, the portable surgery system further comprises: an electronics layer embedded in a wall of the portable enclosure. In some embodiments, the electronics layer comprises a sensor of the one or more sensors. In some embodiments, the electronics layer further comprises a display screen configured to display parameters, pictures or videos recorded by the one or more sensors, data derived from the parameters, pictures or videos recorded by the one or more sensors, or a combination thereof. In some embodiments, the flow tube is configured to provide a higher air pressure in the surgical environment inside the portable enclosure than the user environment outside the portable enclosure.

In some embodiments, a method of training a surgery robot, simulation, or providing reference material for educational purposes may comprise: providing the portable surgical system; receiving data collected from one or more sensors that are disposed in or around the portable surgical system, wherein the portable surgical system comprises at least one motion sensor for detecting a movement of a surgical instrument, a medical professional, a surgery robot, or any combination thereof; generating procedure information based on the data, wherein the procedure information comprises instructions for performing a surgical procedure; and training a control algorithm for controlling the surgery robot using datasets, wherein the datasets are generated using the procedure information.

In some embodiments, the data may comprise structured data, time-series data, unstructured data, relational data, or any combination thereof. In some embodiments, the unstructured data may comprise audio data, image data, video, mechanical data, electrical data, chemical data, and any combination thereof, for use in accurately simulating or training robotics or simulations. In some embodiments, the method may further comprise visual analysis of the surgical environment through infrared, visible light, Terahertz (THz), ultraviolet, gamma rays, millimeter waves, microwaves, x-ray, or any combination thereof. In some embodiments, the method may further comprise audio analysis of the surgical environment through microphones, visual vibration analysis, or both. In some embodiments, the method may further comprise mechanical, electrical, and chemical analysis of the surgical environment using the one or more sensors. In some embodiments, the relational data may comprise data from a customer system, an enterprise system, an operational system, a website, web accessible application program interface (API), or any combination thereof. In some embodiments, the data may be uploaded to a cloud-based database. In some embodiments, the datasets may be uploaded to a cloud-based database. In some embodiments, the datasets may be processed with the intention for training machine learning, artificial intelligence, or other statistically based algorithms.

In some embodiments, the method further comprises combining, integrating, or fusing the data received. In some embodiments, the method further comprises reconstructing 3-dimentional images based on information detected or recorded. In some embodiments, the method further comprises fusing additional data with the 3-dimentional images and constructing hybrid 3-dimentional images. In some embodiments, the data or datasets are processed to produce automatic diagnostic, surgery support, or treatment suggestions based on knowledge bases, expert systems, or other suitable information tools.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Novel features are set forth with particularity in the appended claims. A better understanding of the features and advantages of the present invention will be obtained by reference to the following detailed description that sets forth illustrative embodiments, in which the principles are utilized, and the accompanying drawings (also "figure" and "FIG." herein), of which:

FIG. 8A shows an example of a right side perspective view of a portable environment control system (e.g., an airflow device);

FIG. 8B shows an example of a left side perspective view of the portable environment control system (e.g., an airflow device);

FIG. 8C shows an example of a right side perspective view of a power source (e.g., a battery pack);

FIG. 8D shows an example of a top view of the power source (e.g., a battery pack);

FIG. 8E shows an example of supports;

FIG. 9A shows an example of a perspective view of a packed portable surgical system;

FIG. 9B shows an example of a top view of an unpacked portable surgical system (partially set up);

FIG. 9C shows an example of a bottom view of the unpacked portable surgical system (partially set up);

FIG. 10A is a schematic view of the process of unpacking a packed portable surgical system;

FIG. 10B shows a partial schematic view of the process of unpacking the packed enclosure;

FIG. 10C shows a schematic view of an unpacked portable surgical system (partially set up) over a subject;

FIG. 12A shows a schematic view of an inflated unpacked portable surgery system over a subject;

FIG. 12B shows a schematic view of a sleeve of the portable surgery system;

FIG. 13A shows a partial top view of an inflated unpacked portable surgery system;

FIG. 13B shows a schematic perspective view of the inflated, unpacked portable surgery system;

DETAILED DESCRIPTION

Overview

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Disclosed herein are portable surgical systems. A portable surgical system may be an ultraportable inflatable surgical environment that can fit in a small container (e.g., a backpack). A portable surgical system can be ultraportable, on-demand and rapidly deployable, reducing a patient's exposure to airborne particulates and a provider's exposure to patient-derived fluids. Additional features and advantages of a portable surgical system may include: allowing a user to seal sterile clear system to patient and operates via different ports; fitting into existing workflows; including integrated environmental control systems; fully self-contained; reducing scrub gear requirements; having excellent visual quality; and including reusable components. To use a portable surgical system, a provider can lay a patient on an operating table, unfold a portable enclosure of the portable surgical system, perform preoperative procedures (e.g., skin disinfecting procedure), and place the portable enclosure on top of the patient so that a drape is attached to a surgical site of the patient.

Figure 1:
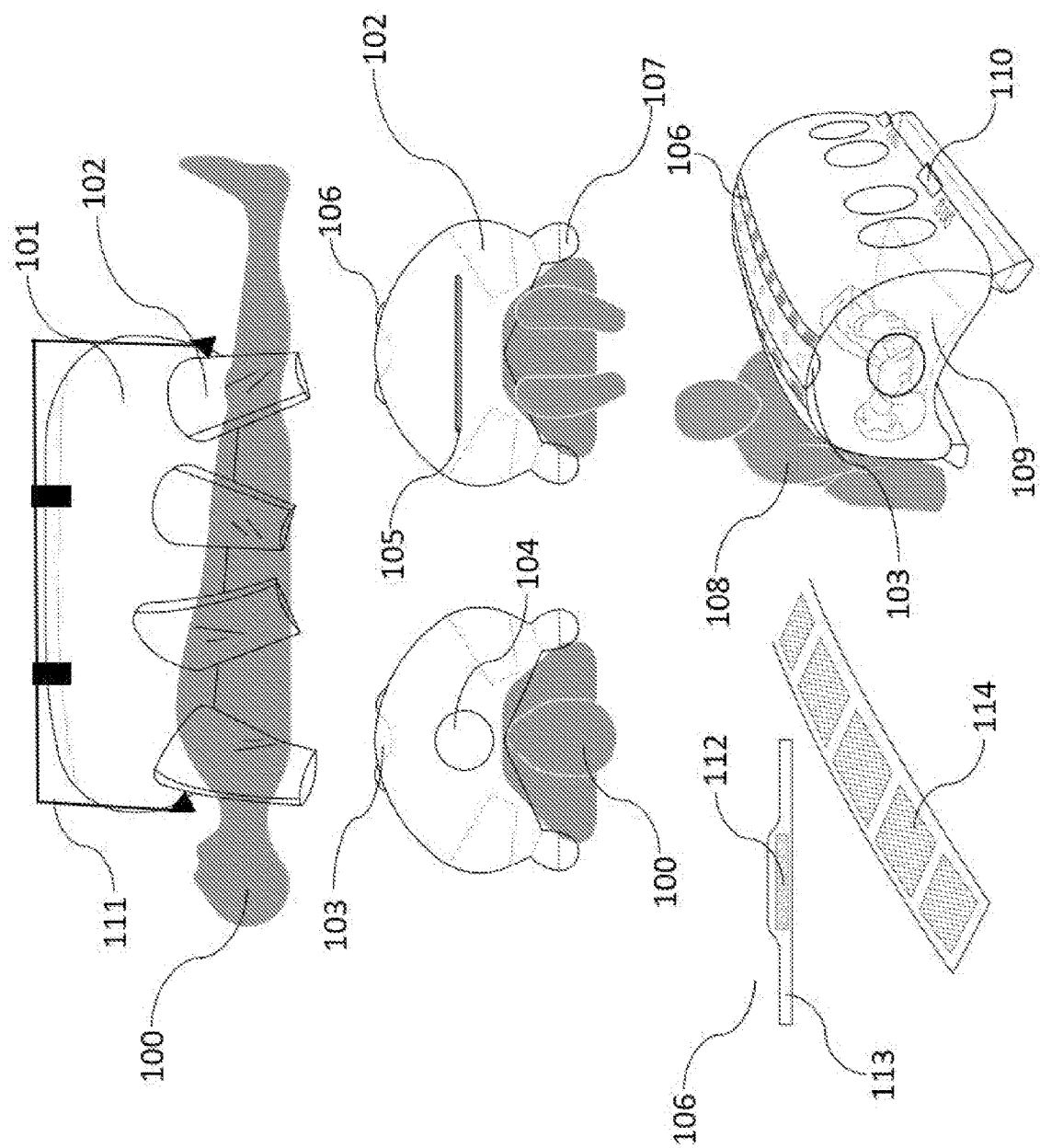
FIG. 1 is an example of an overall view of the surgical system with various features, shown from multiple angles.

FIG. 1 is an example of an overall view of a portable surgical system with various features, shown from multiple angles. A patient 100 can be placed underneath a surgical system. Access to the patient is granted through an adhesive layer (e.g., drape) 109. The adhesive layer 109 is placed onto the patient's skin, and a skilled operator (e.g., provider) 108 would then simultaneously cut through the adhesive layer 109 and patient 100 to begin the surgical procedure. Adhesive layer 109 in this instance contains anti-microbial properties to help ensure a sterile procedure. Alternative to patient 100 access through adhesive layer 109, the patient may place their arms, legs, or head through the port 104. Port 104 would be covered or perforated to maintain a proper sealed barrier between the outside environment and the internal surgical environment and would be removed or broken if needed. In the current preferred embodiment, the patient's extremities or head would be placed through port 104, thereby exposing the patient 100 inside the portable enclosure 101. Port 104 would contain a stretchy material around the border so that when a portion of the patient 100 is placed inside the port, the stretchy material will be stretched around the portion of the patient 100 that is inserted. This stretchy material that is stretched around the patient would create a hermetic, or sufficient, seal between the port 104 and the patient 100, so that the barrier between the outside environment and the internal surgical environment is maintained. Access to the surgical environment by a skilled operator 108 is permitted through sleeves 102. These sleeves may be inverted to allow for easier access or for sterility purposes. Sleeves 102 may also have gloves pre-attached to the ends, so the skilled operator 108 would not need to provide their own gloves.

An optically clear sterile environment 101 is established by a device capable of providing power and clean airflow necessary for maintaining the proper function of the portable enclosure. In the preferred embodiment, this device would allow for the inflation of sterile environment 101. To assist with the structure of the sterile environment 101, a support system (e.g., frame) 111 is mounted externally. Other support mechanisms similar to the support system 111 may be utilized internally, embedded within the surgical environment itself, or used in combination with differing embodiments. Such support systems may include ribs inflated with higher air pressure than the environment, rigid ribs, or internal frames. Sterile airflow is provided through ventilation system (e.g., flow tube) 103, whereby an even laminar flow can be provided to sterile enclosure 101. This ventilation system 103, as designed, will collapse when the pressure inside the ventilation system is less than the pressure within the sterile enclosure 101. Lighting system (e.g., light sources) 106 is placed on top of the sterile environment to provide additional optical clarity. This lighting system 106 can be adhered or placed on top of the sterile environment. The lighting system 106 is made up of lighting element(s) 112 and a material 113. In the preferred embodiment, material 113 is a flexible material with a high coefficient of friction that can be placed on top of the sterile enclosure 101 without worry of sliding or shifting. Other embodiments may utilize magnets or other fixing mechanisms. The lighting system may be comprised of a singular lighting element 112 or multiple lighting elements 114.

Additional access to the sterile environment 101 is permitted in this preferred embodiment through a larger port 105. Port 105 may be fastened by magnets and its seal ensured through an air-filled compartment that surrounds the magnets with the intention to inflate and seal any gaps between the magnets. Other ports 110 display a variety of different ports that allow for the placement of tools or wires that may need to traverse the barrier of sterile enclosure 101. Any fluid or waste material is permitted to gather in reservoirs 107.

Definitions

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated and, when appropriate, fractions thereof (such as one tenth and one hundredth of an integer), unless otherwise indicated.

The terms "one or more" or "at least one" can refer to an individual, can refer to any one member of a group, or can refer to any two or more members of a group, such as, e.g., any $\geq 3$, $\geq 4$, $\geq 5$, $\geq 6$ or $\geq 7$ etc. of said members, and up to all said members.

The term "about" or "approximately" can mean within an acceptable error range for the particular value as determined by one of ordinary skill in the art, which can depend in part on how the value is measured or determined, e.g., the limitations of the measurement system. For example, "about" can mean plus or minus 10%, per the practice in the art. Alternatively, "about" can mean a range of plus or minus 20%, plus or minus 10%, plus or minus 5%, or plus or minus 1% of a given value. Alternatively, particularly with respect to biological systems or processes, the term can mean within an order of magnitude, within 5-fold, or within 2-fold, of a value. Where particular values are described in the application and claims, unless otherwise stated the term "about"

meaning within an acceptable error range for the particular value should be assumed. Also, where ranges and/or subranges of values are provided, the ranges and/or subranges can include the endpoints of the ranges and/or subranges.

The terms "a" and "an" as used herein can refer to "one or more" of the enumerated components unless otherwise indicated or dictated by its context. The use of the alternative (e.g., "or") should be understood to mean either one, both, or any combination thereof of the alternatives.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the disclosure, and vice versa. Furthermore, compositions of the disclosure can be used to achieve methods of the disclosure.

The terms "subject," "individual," or "patient" as used herein can encompass a mammal and a non-mammal. A mammal can be any member of the Mammalian class, including but not limited to a human, a non-human primates such as a chimpanzee, an ape or other monkey species; a farm animal such as cattle, a horse, a sheep, a goat, a swine; a domestic animal such as a rabbit, a dog (or a canine), and a cat (or a feline); a laboratory animal including a rodent, such as a rat, a mouse and a guinea pig, and the like. In some cases, a mammal can be a display animal, a breeding animal, a companion animal, an endangered species, and the like. A non-mammal can include a bird, a fish and the like. In some embodiments, a subject can be a mammal. In some embodiments, a subject can be a human. In some instances, a human can be an adult. In some instances, a human can be a child. In some instances, a human can be age 0-17 years old. In some instances, a human can be age 18-130 years old. In some instances, a subject can be a male. In some instances, a subject can be a female. In some cases, a subject may be a chimera or hybrid. In some instances, a subject can be diagnosed with, or can be suspected of having, a condition or disease. In some instances, a disease or condition can be cancer. A subject can be a patient. A subject can be an individual. A subject can be a user. In some instances, a subject, individual, or patient can be used interchangeably.

It should be understood that when an element or layer is referred to as being "on" or "connected to" another element or layer, it can be directly on or directly connected to the other element or layer, or intervening elements or layers may be present. In contrast, when an element or layer is referred to as being "directly on" or "directly connected to" another element or layer, there are no intervening elements or layers present. It will be understood that for the purposes of this disclosure, "at least one of X, Y, and Z" can be construed as X only, Y only, Z only, or any combination of two or more items X, Y, and Z (e.g., XYZ, XY, YY, YZ, ZZ).

Portable Surgical System in General

A portable surgical system may comprise a transparent, soft plastic portable enclosure which may be attached reversibly around the patient's body immediately encompassing the planned surgical site. A portable enclosure may integrate ports (e.g., arm ports) to allow access to the inside of the portable enclosure. In some cases, a port can allow access to provider arms. In some cases, a port can allow access to augmenting instrumentation taking the place of arms such as laparoscopes or robots. Other ports (e.g., material ports) which can be repeatedly opened and closed may be used to maintain portable enclosure environmental integrity. Ports may allow the passing of anatomical specimens, instruments, and other materials into and out of the portable enclosure during a procedure. A portable enclosure may incorporate into a sterile field particular to a given procedure, one or more sections to hold instrument trays. A portable enclosure may be filled with air from an environmental control system through an inlet, valve, and manifold system integrated into the portable enclosure. An environmental control system may be capable of enacting preselected controls for a given procedure. Preselected controls can include HEPA filtration, humidity modulation, heating or cooling, or change of gas composition. A portable surgical system may be lightweight and may be used in conventional operating rooms to improve sterility. In some circumstances, a portable surgical system may be used where no operating room is available, such as field hospitals.

A portable surgical system may include a disposable component (e.g. a portable enclosure with patient interface), and a reusable component (e.g. an environmental control system and optional external support frame). A disposable component may include an operating section and an instrument section separated from the operating section. An environmental control component may be connected with a portable enclosure such as to control an environment inside the portable enclosure. An external support frame may be configured to connect with a disposable component to provide mechanical support to the disposable component. A support frame may also be built into the disposable component.

A method for using a portable surgical system may include any one of the following steps: laying a patient on top of an operating table; placing an instrument tray holder over patient legs; performing a skin disinfecting procedure; placing a disposable component over a surgical site with an operating-section cranial and instrument-section portion caudal; placing one pair of surgical gloves in a portable enclosure for each planned user at arm ports corresponding to a user's expected position; placing an instrument tray via material port in an instrument-section; engaging an environmental control system; attaching an external frame to an instrument tray holder; pulling tethers from an external top of portable enclosure and securing to a frame in a top clip; and placing arms inside portable enclosure and applying gloves.

In an aspect, a portable surgical system may comprise a portable enclosure and one or more sensors. In some aspects, a portable surgical system designed for interoperability with surgical or research tools and processes may comprise a portable enclosure separating a surgical environment inside the portable enclosure from a user environment outside the portable enclosure. A portable enclosure can comprise a flow tube attached to the inside of the portable enclosure. A flow tube can be connected to an environmental control system. A flow tube can be configured to provide an essentially uniform laminar airflow inside at least part of a portable enclosure. In some aspects, a portable surgical system can comprise one or more sensors. One or more sensors can comprise at least one motion sensor configured to detect a movement of a surgical instrument, a medical professional, a patient, a surgical robot, or any combination thereof. In some aspects, one or more sensors can comprise at least one sensor configured to detect situational or environmental parameters that can comprise patient vitals and diagnostics, humidity, temperature, pressure, brightness, or other information pertinent to the efficacy of the functioning and interoperability of the portable surgical system.

In some aspects, a portable surgical system designed for interoperability with surgical or research tools and processes may comprise a portable enclosure that can comprise: one or more ports allowing for the entry, exit, and insertion of surgical and research tools between the surgical environment and a user environment for interoperable use with the portable surgical system, surgical procedure, surgical personnel, patient, or any combination thereof; and one or more sensors that can comprise at least one motion sensor configured to detect a movement of a surgical instrument, a medical professional, a patient, a surgical robot, or any combination thereof. In some aspects, a portable surgical system designed for interoperability with surgical or research tools and processes may comprise a portable enclosure that can comprise one or more ports allowing for the entry, exit, and insertion of surgical and research tools between the surgical environment and a user environment for interoperable use with the portable surgical system, surgical procedure, surgical personnel, patient, or any combination thereof and one or more sensors that can comprise at least one sensor configured to detect situational or environmental parameters that can comprise patient vitals and diagnostics, humidity, temperature, pressure, brightness, or other information pertinent to the efficacy of the functioning and interoperability of the portable surgical system.

A portable enclosure may be easily assembled and dissembled. A portable enclosure may be formed of biologically acceptable materials suitable for medical applications. A biologically acceptable material may comprise cellophane, vinyl, acetate, polyethylene acrylic, butyl rubber, ethylene-vinyl acetate, natural rubber, a nitrile, silicone rubber, a styrene block copolymer, a vinyl ether, a tackifier, or any combination thereof. A portable enclosure may be formed of a polymeric material. A polymeric material may include one or more polymers. For example, a polymeric material may include one or more of polyvinyl chloride, polyvinylidene chloride, polyethylene, polyisobutene, and poly[ethylene-vinyl acetate] copolymer. A portable enclosure may be formed of a composite material. A composite material may include, for example, a reinforced plastic, a ceramic matrix composite, a metal matrix composite, or any combination thereof.

The size of a portable enclosure may be adjustable. In some embodiments, the size of a portable enclosure after adjustment may be at most about 90%, 80%, 70%, 60%, 50%, 40%, 30%, 20%, 10% or less of the size of the portable enclosure before adjustment. In some embodiments, the size of a portable enclosure after adjustment may be at least about 10%, 20%, 30%, 40%, 50%, 60%, 70%, 80%, 90% or more of the size of the portable enclosure before adjustment.

A portable enclosure may be configured to separate a surgical environment inside the portable enclosure from a user environment outside the portable enclosure. A portable closure may serve as an antimicrobial, antiviral, antipathogenic or antibacterial barrier between a surgical environment and a user environment. A portable enclosure can help to reduce or eliminate contamination of a surgical procedure outside a traditional surgical room. The risk of infections to patients and healthcare personnel can be significantly reduced. A surgical environment may comprise a surgical site of a subject's body. A surgical site may comprise at least a part of a subject's body that needs surgery. A user environment may comprise an environment outside a portable enclosure. An environment outside a portable enclosure may comprise any environment, including a surgical room or a non-surgical place.

A portable enclosure may comprise a flow tube attached to an inside of a portable enclosure and connected to an environmental control system. A flow tube may be formed of the same material as a portable enclosure. A flow tube may be formed of a different material as a portable enclosure. A flow tube may be formed of a biologically acceptable material suitable for medical applications. A biologically acceptable material may comprise cellophane, vinyl, acetate, polyethylene acrylic, butyl rubber, ethylene-vinyl acetate, natural rubber, a nitrile, silicone rubber, a styrene block copolymer, a vinyl ether, a tackifier, or any combination thereof A flow tube may be formed of a polymeric material. A polymeric material may include one or more polymers. For example, A polymeric material may include one or more of polyvinyl chloride, polyvinylidene chloride, polyethylene, polyisobutene, and poly[ethylene-vinyl acetate] copolymer. A flow tube may be formed of a composite material. A composite material may include, for example, a reinforced plastic, a ceramic matrix composite, a metal matrix composite, or any combination thereof.

A flow tube may be configured to provide an essentially uniform laminar airflow inside at least part of a portable enclosure. An essentially uniform airflow may be accomplished by varying the density of perforations in a flow tube in which the density of perforations may be higher at the end of the flow tube closer to the supply of the air and the density of perforations decreases as the distance from the supply increases until the density may be at its lowest value. An essentially uniform air flow may be accomplished when perforation density along the flow tube decreases according to the inverse of an elliptically shaped function. The pressure within an inviscid flow may rise along a streamline if the velocity of the airflow decreases, and in a perforated tube of constant cross sectional area, the velocity within a tube may drop as it passes perforations from which flow may be emanating, as long as the flow may be of nearly constant density which will be the case for flows of air substantially below the speed of sound. The pressure in a perforated tube may rise as the distance from the source increases and, as a result, the rate of flow from each perforation may rise with distance from the source assuming the perforations are of constant cross-sectional area (see PCT/US2017/042266).

An environmental control system may include a HEPA filter, a fan (blower with motor), a filter-blower adapter, a battery, or a control section. In some cases, a HEPA filter, a fan, a filter-blower adapter, a battery, or a control section may be connected to a portable enclosure via sterile flexible tubing. In some cases, a HEPA filter, a fan, a filter-blower adapter, a battery, or a control section connected to a portable enclosure via sterile flexible tubing may be collectively referred to as air supply system. A battery may be disposable or rechargeable. In some aspects, a system can run off an electrical grid if the procedure occurs in a setting in which this is possible. An air supply system may be connected to a flexible overhead tube of a surgical portable enclosure with flexible tubing so that the inlet height of the overhead airflow tube can adjust based on the level of inflation of the portable enclosure. A HEPA filter immediately downstream of air inflow may be changeable and customizable such that it provides one or more other controls based on procedural need. A control can include a humidity modulator filter, a gas content with supply of medical gases, and/or a temperature modulator with heat/cold sinks. An air supply system may include an electrical fan, a manual pump, or both. A manual pump may provide redundancy and may be used in the event of unavailability of electrical power supply or to provide higher flows without expending electrical power. A manual pump can be implemented in any number of mechanical setups, including, but not limited to: via manual or pedal bellows-style pump or other general positive displacement pump, or manual or pedal rotary pump. An air supply system may further include one or more one-way valves which allow air from either only the electrical fan or only the manual pump to flow toward a plastic portable enclosure. A filter may be downstream of both electrical and manual air supply. An external air supply system may connect to the portable enclosure.

A portable surgical system may comprise at least one motion sensor configured to detect a movement of a surgical instrument, a medical professional, a subject, a surgery robot, or any combination thereof. A motion sensor may comprise an infrared sensor, an optical sensor, a microwave sensor, an ultrasonic sensor, a radio-frequency sensors, a magnetic sensor, a vibration sensor, an acceleration sensor, a gyroscopic sensor, a tilt sensor, a piezoelectric sensor, a pressure sensor, a strain sensor, a flex sensor, an electromyographic sensor, an electrocardiographic sensor, an electroencephalographic sensor, a thermal sensor, a capacitive touch sensor, a resistive touch sensor, an acoustic sensor, a sound sensor, a vibration sensor, a chemical sensor, an electric current sensor, a magnetic sensor, a radio sensor, a moisture sensor, a humidity sensor, a flow sensor, a radiation sensor, an imaging sensor, a light sensor, an optical sensor, a pressure sensor, a density sensor, a thermal sensor, a heat sensor, a temperature sensor, a proximity sensor, or any combination thereof. A sensor may comprise at least one sensor configured to detect situational or environmental data including, but not limited to, patient vitals and diagnostics, humidity, temperature, pressure, brightness, or other information pertinent to the efficacy of the functioning and interoperability of the surgical system.

A portable enclosure system may comprise one or more ports allowing for the entry, exit, and insertion of surgical and research tools between the surgical environment and a user environment for interoperable use with the portable surgical system, surgical procedure, surgical personnel, patient, or any combination thereof. A surgical and research tool may comprise a stethoscope, a suction device, a thermometer, a tongue depressor, a transfusion kit, a tuning fork, a ventilator, a watch, a stopwatch, a weighing scale, a crocodile forceps, a bedpan, a cannula, a cardioverter, a defibrillator, a catheter, a dialyser, an electrocardiograph machine, enema equipment, an endoscope, a gas cylinder, a gauze sponge, a hypodermic needle, a syringe, an infection control equipment, an instrument sterilizer, a kidney dish, a measuring tape, a medical halogen penlight, a nasogastric tube, a nebulizer, an ophthalmoscope, an otoscope, an oxygen mask and tubes, a pipette, a dropper, a proctoscope, a reflex hammer, a sphygmomanometer, or any combination thereof.

A portable enclosure system may comprise a processor configured to process data collected from one or more sensors. The data may comprise structured data, time-series data, unstructured data, relational data, or any combination thereof. Unstructured data may comprise text, audio data, image data and/or video. Time-series data may comprise data from one or more of a smart meter, a smart appliance, a smart device, a monitoring system, a telemetry device, or a sensor. Relational data may comprise data from one or more of a customer system, an enterprise system, an operational system, a website, or web accessible application program interface (API). A process of collecting data may be done by a user through any method of inputting files or other data formats into software or systems.

A portable surgical system may comprise a data ingestion module configured to ingest data into a processing component. A data ingestion module may be configured to retrieve or receive data from one or more data sources. In some cases, retrieving data can comprise a data extraction process. In some cases, receiving data can comprise receiving transmitted data from an electronic source of data. A platform may be configured to retrieve data, receive data, or both, from many different data sources such as wearable devices, cameras, smartphones, laptops, databases, or cloud storage systems.

Data may be stored in a database. A database can be stored in computer readable format. A database may comprise an external database. An external database may be a medical database, including, but not limited to, Adverse Drug Effects Database, AHFS Supplemental File, Allergen Picklist File, Average WAC Pricing File, Brand Probability File, Canadian Drug File v2, Comprehensive Price History, Controlled Substances File, Drug Allergy Cross-Reference File, Drug Application File, Drug Dosing & Administration Database, Drug Image Database v2.0/Drug Imprint Database v2.0, Drug Inactive Date File, Drug Indications Database, Drug Lab Conflict Database, Drug Therapy Monitoring System (DTMS) v2.2/DTMS Consumer Monographs, Duplicate Therapy Database, Federal Government Pricing File, Healthcare Common Procedure Coding System Codes (HCPCS) Database, ICD-10 Mapping Files, Immunization Cross-Reference File, Integrated A to Z Drug Facts Module, Integrated Patient Education, Master Parameters Database, Medi-Span Electronic Drug File (MED-File) v2, Medicaid Rebate File, Medicare Plans File, Medical Condition Picklist File, Medical Conditions Master Database, Medication Order Management Database (MOMD), Parameters to Monitor Database, Patient Safety Programs File, Payment Allowance Limit-Part B (PAL-B) v2.0, Precautions Database, RxNorm Cross-Reference File, Standard Drug Identifiers Database, Substitution Groups File, Supplemental Names File, Uniform System of Classification Cross-Reference File, or Warning Label Database.

A portable surgical system can comprise a processor or a plurality of processors for parallel processing. A processor may comprise a central processing unit (CPU). A processor can be a single core or multi core processor. A processor may be configured to access data stored in a computer readable memory. A computer system may be used to analyze data to obtain a result. A result may be stored remotely or internally on storage medium, and communicated to personnel such as medication professionals. A computer system may be operatively coupled with components for transmitting a result. Components for transmitting can include wired and wireless components. Examples of wired communication components can include a Universal Serial Bus (USB) connection, a coaxial cable connection, an Ethernet cable such as a Cat5 or Cat6 cable, a fiber optic cable, or a telephone line. Examples or wireless communication components can include a Wi-Fi receiver, a component for accessing a mobile data standard such as a 3G or 4G LTE data signal, or a Bluetooth receiver. In some embodiments, data in a storage medium may be collected and archived to build a data warehouse.

A portable enclosure may comprise features for user entry and to enable manipulation of the environment within a portable enclosure. Features for user entry and to enable manipulation of the environment within the portable enclosure may comprise one or more ports. A portable enclosure may include two major types of ports. A first type of port may be an arm port, which may allow access to the inside of the enclosure by either provider arms or augmenting instrumentation taking the place of arms such as laparoscopes or robots. The number of arm ports may be at least about 1, 2, 3, 4, 5, 6, 7, 8, 9, 10, 15, 20 or greater. In some cases, the number of arm ports may be at most about 20, 15, 10, 9, 8, 7, 6, 5, 4, 3, 2, 1 or less.

An arm port may be a simple opening in the side of the enclosure which seals reversibly against user arms. An arm port may be a sleeve that is a hollow cylinder or frustrated cone of impermeable plastic that tapers toward the inside of the enclosure away from a wall. The length of a sleeve may be adequate to permit ergonomic handoff of instruments among ports at contralateral ends of the system. The material of a sleeve may be the same as the one used for an enclosure side, or it can be a different one, such as a material used in surgical gown sleeves. A sleeve end may be free or may incorporate a cuff of elastic material to fit against a user wrist. A sleeve may be made of two or more distinct layers. A layer may serve as an outer layer, an inner layer, or both. In an embodiment, an outer layer can be chosen for its ability to serve as an external layer with focus on ergonomics, ease of use, or functional properties (see U.S. 62/670,891).

An arm port may be with a sleeve may end in a glove. A port on an enclosure may be a materials port, which may allow an instrument tray and instruments to be moved into the enclosure prior to a procedure. Additionally, a port may allow materials to be moved in and out of the enclosure throughout the surgical procedure (see PCT/US2017/042266).

A portable enclosure may comprise features for fluid retention away from the surgical site. Features for fluid retention away from the surgical site may comprise one or more reservoirs as part of a portable enclosure. In some cases, one or more reservoirs may not be part of a portable enclosure. One or more reservoirs may be placed at the bottom of a portable enclosure when a portable enclosure is in use. A portable enclosure can include at least about 1, 2, 3, 4, 5, 6, 7, 8, 9, 10, 15, 20 or greater reservoirs. In some cases, the number of reservoirs may be at most about 20, 15, 10, 9, 8, 7, 6, 5, 4, 3, 2, 1 or less.

A portable enclosure may comprise features for attachment or the securing of the portable enclosure to the patient. Features for attachment or the securing of the portable enclosure to the patient may comprise a drape or frames.

A drape may be an incise drape. A panel of incise drape may be incorporated into the bottom of a portable enclosure. An incise drape may serve as an interface with a patient body. The size and shape of an incise drape may be configured to cover the surgical site on the patient's body while essentially excluding body surface outside the surgical site. Consequently, only the surgical site of a patient's body (i.e. area covered by the incise drape) may be included within a portable enclosure, while the remainder of the patient body may be excluded from the sterile field. By excluding from the portable enclosure the unnecessary body surface, the efficacy of the system may be significantly improved since a patient's body surface contributes to environment contamination inside an enclosure. Exclusion of high-contaminant regions such as the oropharynx or the genitals may significantly improve the efficacy of the system. A portable enclosure may include incise drapes of different shapes and sizes and may be disposed at different positions on the portable enclosure such as to fit the needs of different types of medical procedures. The bottom corners of a portable enclosure may include straps for securing the enclosure to the patient or to the operating table for additional stability.

Frames may include a central frame and tethers to support a portable enclosure in the case of a sudden pressure loss. A central frame may be lightweight and/or collapsible so as to be easily transported. A frame may be made of a rigid material, such as plastic, rigid polyvinyl tubes, aluminum tubing, and other materials familiar to practitioners knowledgeable in the field. A frame may include four oblique tubes which are reversibly secured to the instrument tray holder or operating table such that the instrument tray holder or operating table form the bottom of a pentagon when viewed axially. One or more of these pieces may be connected to one another via custom connectors or hinges, configured to maintain the pentagon within the same plane. The topmost vertex of a frame may be reversibly attached to the disposable component top, such as via a formed plastic slot in the disposable component or via tether only. Various other tether arrangements may be utilized to optimize support from the central frame (see PCT/US2017/042266). Such support may be provided by other types of supportive structures. Other types of supportive structures may be built of a flexible, non-rigid material that utilizes air pressure to maintain turgidity. The supportive structure may comprise inflatable supports. The inflatable supports may be inflated through either a port common to the air-supply system of an environmental control system or a separate system utilizing a secondary air supply. The secondary air supply may comprise a secondary pump, mechanical pump, blown by a user, or any combination thereof. The inflatable supports may or may not have valves to keep pressure without additional user intervention. The additional user intervention may comprise user's actions of tying the supports up or securing the supports. The supportive structures may be built into the disposable enclosure directly or attached via clamps, adhesive, clips, or other mechanical means.

A portable enclosure may comprise features for allowing a direct incision to be performed through the boundaries of the portable enclosure and the patient's body simultaneously.

A portable device may provide power and sterile or substantially clean airflow for the portable enclosure. Power may be supplied by an onboard power source, comprising a disposable battery, a rechargeable battery, a solar-powered source, a wind-powered source, a hydraulically powered source, a combustion powered source, an electrochemically powered source, a radioactively powered source, or any combination thereof. Power may be supplied by an external source, comprising a one-time use battery, a rechargeable battery, power from an established electrical grid, or any combination thereof. Due to the substantially clean airflow, an airborne particulate level inside the portable enclosure may be at most about 100,000 particles/$m^3$, 90,000 particles/$m^3$, 80,000 particles/$m^3$, 70,000 particles/$m^3$, 60,000 particles/$m^3$, 50,000 particles/$m^3$, 40,000 particles/$m^3$, 30,000 particles/$m^3$, 20,000 particles/$m^3$, 10,000 particles/$m^3$, 5,000 particles/$m^3$, 4,000 particles/$m^3$, 3,000 particles/$m^3$, 2,000 particles/$m^3$, 1,000 particles/$m^3$, 500 particles/$m^3$ or less. In some cases, the airborne particulate level inside the portable enclosure may be at least 500 particles/$m^3$, 1,000 particles/$m^3$, 2,000 particles/$m^3$, 3,000 particles/$m^3$, 4,000 particles/$m^3$, 5,000 particles/$m^3$, 10,000 particles/$m^3$, 20,000 particles/$m^3$, 30,000 particles/$m^3$, 40,000 particles/$m^3$, 50,000 particles/$m^3$, 60,000 particles/$m^3$, 70,000 particles/$m^3$, 80,000 particles/$m^3$, 90,000 particles/$m^3$, 100,000 particles/$m^3$ or more.

A portable enclosure may be flexible with high optical clarity. The total transmittance of the portable enclosure may be at least about 50%, 55%, 60%, 65%, 70%, 75%, 80%, 85%, 90%, 91%, 92%, 93%, 94%, 95%, 96%, 97%, 98%, 99% or greater. In some cases, a total transmittance of the portable enclosure may be at most about 99%, 98%, 97%, 96%, 95%, 94%, 93%, 92%, 91% or greater.

An environmental control system may be configured to supply air to the flow tube and to provide sterile or markedly cleaner conditions inside the portable enclosure. Sterile or markedly cleaner conditions may comprise a condition with an airborne particulate level of at most about 100,000 particles/$m^3$, 90,000 particles/$m^3$, 80,000 particles/$m^3$, 70,000 particles/$m^3$, 60,000 particles/$m^3$, 50,000 particles/$m^3$, 40,000 particles/$m^3$, 30,000 particles/$m^3$, 20,000 particles/$m^3$, 10,000 particles/$m^3$, 5,000 particles/$m^3$, 4,000 particles/$m^3$, 3,000 particles/$m^3$, 2,000 particles/$m^3$, 1,000 particles/$m^3$, 500 particles/$m^3$ or less. In some cases, sterile or markedly cleaner conditions may comprise a condition with an airborne particulate level inside of at least about 500 particles/$m^3$, 1,000 particles/$m^3$, 2,000 particles/$m^3$, 3,000 particles/$m^3$, 4,000 particles/$m^3$, 5,000 particles/$m^3$, 10,000 particles/$m^3$, 20,000 particles/$m^3$, 30,000 particles/$m^3$, 40,000 particles/$m^3$, 50,000 particles/$m^3$, 60,000 particles/$m^3$, 70,000 particles/$m^3$, 80,000 particles/$m^3$, 90,000 particles/$m^3$, 100,000 particles/$m^3$ or more.

A flow tube may be disposed above a surgical site of a patient's body. A flow tube may be flexible. A flexible tube may be configured to act as a valve system, such as to prevent air backflow from the surgical portable enclosure into the fan and filter. A flexible tube may be in an expanded state when air is blown from the air supply system into a surgical portable enclosure. A flexible tube may be in a collapsed state when air pressure inside a portable enclosure is pushing air from the portable enclosure towards outside a portable enclosure. A collapsed tube may prevent air from exiting a portable enclosure. A tube may be made of flexible material such as to switch from open to close state, and vice versa, based on airflow. When there is net positive airflow through a tube toward the manifold in this configuration, a transmural pressure may be positive relative to the portable enclosure, and a tube is forced open.

A flow tube may be a collapsible tube configured to maintain an open state while airflow through the collapsible tube exerts radial outward pressure sufficient to overcome radial inward pressure of the portable enclosure. An outward pressure sufficient to overcome radial inward pressure of the portable enclosure may be at least about 1.1 times, 1.2 times, 1.5 times, 1.6 times, 1.8 times, 1.9 times, 2 times, 2.1 times, 2.2 times, 2.3 times, 2.4 times, 2.5 times, 2.6 times, 2.7 times, 2.8 times, 2.9 times, 3 times, or greater of the inward pressure of a portable enclosure. An outward pressure sufficient to overcome radial inward pressure of a portable enclosure may be may be at most about 3 times, 2.9 times, 2.8 times, 2.7 times, 2.6 times, 2.5 times, 2.4 times, 2.3 times, 2.2 times, 2.1 times, 2.0 times, 1.9 times, 1.8 times, 1.7 times, 1.6 times, 1.5 times, 1.4 times, or less of an inward pressure of a portable enclosure. A flow tube may be a collapsible tube configured to maintain a closed state when an airflow through a collapsible tube is low such that pressure exerted by the airflow is less than the radial inward pressure of the portable enclosure. In this situation, pressure exerted by an airflow may be at most about 90%, 80%, 70%, 60%, 50%, 40%, 30%, 20%, 10% or less of radial inward pressure of a portable enclosure. In some embodiments, pressure exerted by the airflow may be at least about 10%, 20%, 30%, 40%, 50%, 60%, 70%, 80%, 90% or more of radial inward pressure of a portable enclosure.

An open or closed state of the collapsible tube may serve as an indicator of airflow status of the portable enclosure. The shape of the collapsible tube (whether the tube is inflated or collapsed) may indicate the airflow status. An airflow status may comprise flow rate, pressure, purity, or any combination thereof. When a collapsible tube is inflated, pressure of the airflow may be high in a portable enclosure. When a collapsible tube is collapsed, pressure of the airflow may be low in a portable enclosure.

At least one environmental sensor may be used to detect one or more surgical environment parameters. Surgical environmental parameters may comprise temperature, pressure, humidity, luminance, heart rate, breathing rate, blood pressure, blood oxygen saturation, electrocardiography, electromyography, skin conductance, EBL (Estimated Blood Loss), airflow, air quality, internal and external gas composition, a chemical composition of the surgical environment, or any combination thereof.

A motion sensor may comprise an infrared sensor, optical sensor, microwave sensor, ultrasonic sensor, radio-frequency sensors, magnetic sensor, vibration sensor, acceleration sensor, gyroscopic sensor, tilt sensor, piezoelectric sensor, pressure sensor, strain sensor, flex sensor, electromyographic sensor, electrocardiographic sensor, electroencephalographic sensor, thermal sensor, capacitive touch sensor, resistive touch sensor, or any combination thereof.

A processor may be configured to provide instructions to a surgery robot, provide instructions or alerts to a user of a portable enclosure, provide instructions for devices that are designed to be used with a portable enclosure or standard surgical procedures, collect data for use in robotic control, collect data for use in research, collect data for use in quality control and improvement, or any combination thereof.

Instructions may comprise information related to a surgical procedure. A surgical procedure may comprise appendectomy, breast biopsy, carotid endarterectomy, cataract surgery, cesarean section, cholecystectomy, coronary artery bypass, debridement of wound, dilation and curettage, free skin graft, hemorrhoidectomy, hysterectomy, hysteroscopy, inguinal hernia repairs, low back pain surgery, mastectomy, partial mastectomy, spinal disk fusion, spinal related surgeries, amputations, fracture fixations (internal and external), joint repair and replacement, modified radical mastectomy surgery, radical mastectomy, partial colectomy, prostatectomy, releasing of peritoneal adhesions, tonsillectomy, or any combination thereof. Information related to a surgical procedure may comprise preparation for a surgery, performing tests before a surgery, instructions on how to perform surgery, a recovery process, or any combination thereof.

Information related to a surgical procedure may be stored. Information may be transferred with a patient operated on with the intention to maintain continuity of care. Each patient may be paired with his/her own customized surgical procedure. A customized surgical procedure may be identified by a patient identity, so that a patient can retrieve his/her customized surgical procedure from a storage or a server through a patient identity. A patient identity may comprise patient's photo, name, address, social security number, birthday, telephone number, zip code, or any combination thereof. A patient identity may be encrypted and encoded in a visual graphical code. A visual graphical code may be a one-time barcode that can be uniquely associated with a patient identity. A barcode may be a UPC barcode, EAN barcode, Code 39 barcode, Code 128 barcode, ITF barcode, CodaBar barcode, GS1 DataBar barcode, MSI Plessey barcode, QR barcode, Datamatrix code, PDF417 code, or an Aztec barcode. A visual graphical code may be configured to be displayed on a display screen. A barcode may comprise QR that can be optically captured and read by a machine. A barcode may define an element such as a version, format, position, alignment, or timing of the barcode to enable reading and decoding of the barcode. A barcode can encode various types of information in any type of suitable format, such as binary or alphanumeric information. A QR code can have various symbol sizes as long as the QR code can be scanned from a reasonable distance by an imaging device. A QR code can be of any image file format (e.g. EPS or SVG vector graphs, PNG, TIF, GIF, or JPEG raster graphics format).

A portable surgical system may comprise an information storage unit. An information storage unit can comprise handwriting, phonographic recording, magnetic tape, optical disk, floppy disk, semiconductor storage, floating-gate transistor storage, punched card, paper tape, DNA, RNA, or any combination thereof. An information storage unit may be a non-volatile storage media. A non-volatile storage media may include, for example, optical or magnetic disks, such as any of the storage devices in any computer(s) or the like, such as may be used to implement the databases, etc. shown in a drawing. An information storage unit may be a volatile storage media. A volatile storage media may include dynamic memory, such as main memory of such a computer platform.

A portable surgical system may comprise a transfer unit configured to transfer information between operators. The transfer unit may be a tangible transmission media. A tangible transmission media can include a coaxial cable, a copper wire or fiber optics; including wires that can comprise a bus within a computer system. A transfer unit may be a carrier-wave transmission media. A carrier-wave transmission media may take the form of an electric or an electromagnetic signal, an acoustic wave, or a light wave such as those generated during radio frequency (RF) or infrared (IR) data communications. A tangible transmission media may be a computer-readable media. Computer-readable media may include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution. A transfer unit may transfer information through wireless transfer via frequencies of ELF, SLF, ULF, VLF, LF, MF, HF, VHF, UHF, SHF, EHF, THF, or any combination thereof.

A portable surgical system may further comprise a physical information unit separated from a data collection device (e.g., processor). A physical information unit to be transferred may be programmed by a data collection device either through direct or wireless connection. A connection may be a network. A network can include, a wireless network, a wired network, a local area network (LAN), a Wide Area Network (WAN), a Bluetooth network, a Near Field Communication (NFC) network, or any other type of network that can provide communications between one or more components of a network layout. In some embodiments, a network may be implemented using a cellular and/or a pager network, satellite, licensed radio, or a combination of licensed and unlicensed radio. A network may be wireless, wired (e.g., Ethernet), or a combination thereof.

A physical information unit may be paired with a patient during their transfer to a different healthcare provider through a wristband, dog tag, programmable implant, or other relevant physical medium. A physical information unit may be paired with a patient during their transfer to a different healthcare provider through a wearable device, smartphones, or laptop.

A portable surgical system may further comprise a drape; one or more ports; one or more outlets for exhaust; one or more wire tubes; one or more supportive structures; one or more magnifying lenses; one or more suction components; one or more light sources; or any combination thereof.

An outlet or exhaust may be configured to allow for the release of and changing of air contained within a sterile environment. The number of outlet or exhaust may be at least 1, 2, 3, 4, 5, 6, 7, 8, 9, 10, or greater. The number of outlet or exhaust may be at most 10, 9, 8, 7, 6, 5, 4, 3, 2, 1. An outlet or exhaust may be a perforation between the internal and external environment covered by a filter or porous material. Porous materials may comprise microporous materials, mesoporous materials, macroporous materials, or any combination thereof. An outlet or exhaust may be covered by a pressure-sensitive valve, covered by a one-way valve; or any combination thereof.

A drape may be configured to be disposed on or around a surgical site of a patient's body. A drape may be configured to expose a surgical site. A drape may create a barrier between a surgical field and possible sources of microbes. A drape may minimize microbial migration and contamination from nonsterile to sterile areas by isolating an incision site. A drape may protect a patient from their own skin flora and surgical team members and environment. A drape may be an incise drape as described herein.

A supportive structure may be part of a supportive system. A supportive structure may be designed to maintain a usable volume within a device. The usable volume may be at most about 90%, 80%, 70%, 60%, 50%, 40%, 30%, 20%, 10% or less of the maximum volume of a portable enclosure. In some embodiments, the usable volume may be at least about 10%, 20%, 30%, 40%, 50%, 60%, 70%, 80%, 90% or more of the maximum volume of a portable enclosure.

A supportive structure may be created with spring steel and built into a device's borders and seams; may be created with a rigid pole or rod that can be collapsible or foldable; may be inflatable with an inflatable system that shares the pressure of internal space within the device; or any combination thereof. The supportive structure may be inflatable supports. The inflatable supports are described elsewhere herein. A supportive structure may be a frame. A supportive structure may be formed of a metallic (or metal-containing) material. A metallic material may include one or more elemental metals. For example, a metallic material may include one or more of aluminum, copper, titanium, iron, steel, tin, tungsten, molybdenum, tantalum, cobalt, bismuth, cadmium, titanium, zirconium, antimony, manganese, beryllium, chromium, germanium, vanadium, gallium, hafnium, indium, niobium, rhenium and thallium, and their alloys. A supportive structure may be formed of a polymeric material. A polymeric material may include one or more polymers. For example, a polymeric material may include one or more of polyvinyl chloride, polyvinylidene chloride, polyethylene, polyisobutene, and poly[ethylene-vinylacetate] copolymer. A supportive structure may be formed of a composite material. A composite material may include, for example, a reinforced plastic, a ceramic matrix composite, a metal matrix composite, or any combination thereof.

A portable surgical system may comprise one or more built-in magnifying glasses. In some cases, a portable surgical system may comprise one or more magnifying glasses that may not be built-in. A magnifying glasses may have a focal length of at least 10 cm, 15 cm, 25 cm, 30 cm, 35 cm, 40 cm, 45 cm, 50 cm, 55 cm, 60 cm, 65 cm, 70 cm or greater. In some cases, the magnifying glasses may have a focal length of at most 70 cm, 65 cm, 55 cm, 50 cm, 45 cm, 40 cm, 35 cm, 30 cm, 25 cm, 20 cm, 15 cm, 10 cm or greater.

A portable surgical system may comprise one or more suction components that are formed of absorbent material. A suction component may be placed in reservoirs of a portable enclosure. A suction component may be placed inside a portable enclosure but not in a reservoir. An absorbent material may comprise a sponge, cotton, a cloth, a fabric, a tissue, a paper towel, an absorbent mat, a pad, a pillow, a roll, or any combination thereof.

The portable surgical system may comprise one or more light sources. Light sources may be homogenous light, which offers good illumination on a flat, narrow or deep surface in a cavity, despite obstacles such as surgeons' heads or hands. A central illuminance of the light sources may be between 160,000 and 40,000 lux. The $D_{50}$ diameter of the light source may be at least 50% of $D_{10}$. A color rendering index (Ra) of a light source may be between 85 and 100. Light sources may be connected to a backup power supply so they can be restored within 5 seconds with at least 50% of the previous lux intensity, and within 40 seconds with full lux intensity.

Light sources may comprise lighting elements. The lighting elements may be flexible or substantially flexible. A flexible material can be a material that can be conformed to a shape, twisted, or bent without experiencing plastic deformation. This can enable lighting elements to be used in various settings, such as settings in which contact area with a portable disclosure is important.

Any components of a portable surgical system (e.g., ports, frame, one-way pressure sensitive valve) can be formed of a flexible material. A flexible material can be a material that bends at an angle of least about 1°, 5°, 10°, 15°, 20°, 25°, 30°, 35°, 40°, 45°, 50°, 60°, 70°, 80°, 90°, 100°, 120°, 130°, 140°, 150°, 160°, 170°, or 180° relative to a measurement plane without experiencing plastic deformation or breaking. The flexible material can bend under an applied force over a given area of the flexible material (i.e., pressure). Plastic deformation can be measured by, for example, three-point testing or tensile testing. As an alternative or in addition to, the flexible material can be a material that bends at an angle of least about 1°, 5°, 10°, 15°, 20°, 25°, 30°, 35°, 40°, 45°, 50°, 60°, 70°, 80°, 90°, 100°, 120°, 130°, 140°, 150°, 160°, 170°, or 180° relative to a measurement plane at a plastic deformation that is less than or equal to about 20%, 15%, 10%, 5%, 1%, or 0.1% as measured by three-point testing (e.g., instron extension) or tensile testing. A flexible material can be a substantially pliable material. A flexible material can be a material that can conform or mold to a surface. Such materials can be employed for use in various settings, such as consumer and industrial settings.

A portable surgical system may comprise a device capable of providing power and clean airflow necessary for maintaining the proper function of the portable enclosure and its interoperability with other surgical or research functions. Power may be supplied by an onboard power source, comprising a disposable battery, a rechargeable battery, a solar-powered source, a wind-powered source, a hydraulically powered source, a combustion powered source, an electrochemically powered source, a radioactively powered source, or any combination thereof. Power may be supplied by an external source, comprising a one-time use battery, a rechargeable battery, power from an established electrical grid, or any combination thereof.

A clean airflow to a portable enclosure may be provided by a mechanical filtration. A mechanical filtration may comprise a fiberglass filter, a polyester filter, a High Efficiency Particulate Air (HEPA) filter, an Ultra-Low Penetration Air (ULPA) filter, a carbon filter, a ceramic filter, a demister, sedimentation chamber, cyclone separator, rotating scrubber, venturi scrubber, spray chamber, or any combination thereof. A mechanical filtration may physically remove particles and waste matter from a portable enclosure. Mechanical filtration may use a fine medium such as cotton, dacron, and other synthetic materials to trap detritus, dead plant matter, and other debris.

An electrical filtration may be used to provide clean airflow to a portable enclosure. An electrical filtration may comprise an ionic filter, UV filter, radiation filter, heat-treated filter, dry electro filter, wet electro filter, or any combination thereof. An electrostatic filter may comprise polarized fibers, which may create an electric field that ionizes particles that pass through it. An electronic filter can be passive, active, analog, digital, high-pass, low-pass, band-pass, band-stop, all-pass, discrete-time (sampled), continuous-time, linear or non-linear, infinite impulse response (IIR type), finite impulse response (FIR type). In some cases, a combination of mechanical and electrical filtration can be used.

The portable surgical system may include various monitors, sensors, and/or detectors for detecting/monitoring the subject of the surgical operation, the operators and the operation theatre. It may include additional device for recording and processing the collected information from the monitors, sensors, and/or detectors. In some embodiments, the collected information may include data fusion from multiple sources of the monitors, sensors, and/or detectors, including, for example, cameras operating at different wavelengths or at different positions relative to the portable surgical system. In some embodiments, one or more video cameras or systems of video cameras for 3-dimentional (3D) vision may be placed inside or outside or both inside and outside the portable enclosure. The one or more video cameras or systems of video cameras may include light intensity operating cameras and time of flight (TOF) cameras. The cameras may use visible light as the light source. The cameras may use infrared, ultraviolet or terahertz waves, or ultrasounds as the light source. The cameras in the system of cameras may be placed such that they may continuously monitor the hands or movements of the operator, the position of the surgical instruments used by the operator, and/or the operated zone. The cameras may use different electromagnetic radiation frequency bands or combinations of frequency bands, or ultrasounds, and a data fusion system may be employed to improve the information obtained from the video cameras or systems of cameras.

The one or more time-of-flight (TOF) cameras based on electromagnetic radiation or the systems of cameras may be used to extract the geometric position and 3D surfaces of the operated zones, surgical instruments used, and/or the hands of the operator. The TOF cameras may operate at a wavelength range where the lighting of the enclosure has low intensity to reduce interference and the saturation of the receiving sensors in the camera. The calibration and error correction of the TOF camera may be performed in the portable enclosure with the light sources turned on and positioned as in an operation situation.

Figure 14:
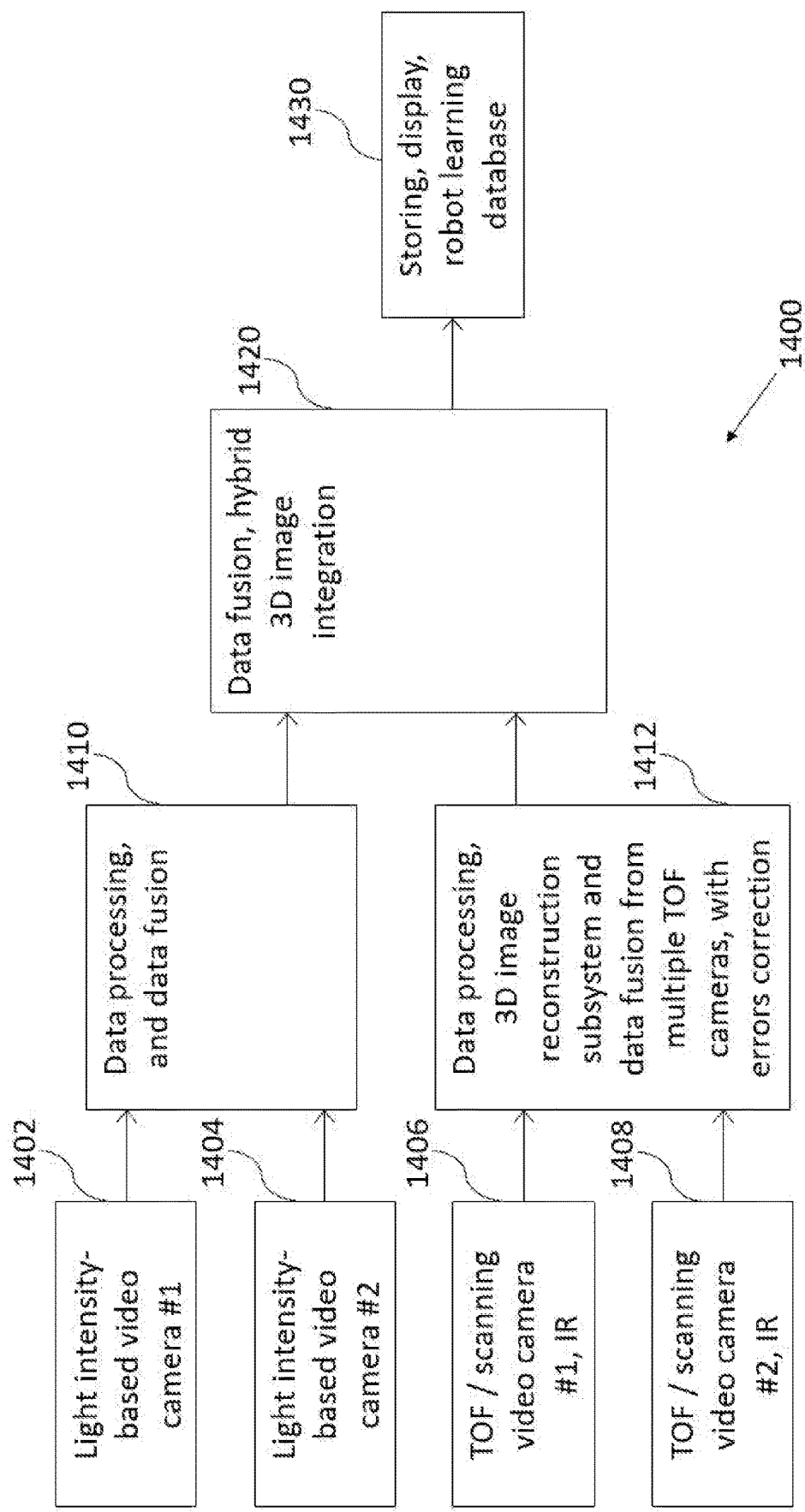
FIG. 14 shows a diagram of the process to record, monitor, and process data from the surgical environment.

The information from the light-intensity based cameras and TOF cameras may be supplied to a data processing system and a data fusion system, respectively, for TOF cameras to data processing, 3D image reconstruction and data fusion from multiple TOF cameras, with automatic errors correction. The information so extracted may be further used for data fusion and hybrid 3D image integration. The results may be used for display and for the database for surgical robots training. FIG. 14 shows a diagram depicting a process 1400 of using some components of the portable surgical system and/or other related system(s) to analyze data.

As shown in FIG. 14, the portable enclosure may use one or more video cameras 1402-1404 or systems of video cameras for 3D vision (not shown) to continuously monitor the three-dimensional positions of the surgical devices used by the operator, where the cameras used may be placed inside or outside the portable enclosure; may be based on intensity (1402 and 1404), or based on time-of-flight (TOF) imaging (1406 and 1408); and may use visible light (1402 and 1404), infrared (1406 and 1408), ultraviolet, terahertz electromagnetic waves, or ultrasounds, or combinations thereof as the light source. The cameras may send detected signals and/or the received/derived information to a computing system. For example, at step 1410, some data detected by the cameras 1402 and 1404 can undergo data processing and data fusion. At step 1412, some data detected by the cameras 1406 and 1408 can undergo data processing, 3D image reconstruction and data fusion, and data correction. At step 1420, the results obtained at steps 1410 and 1412 can undergo data fusion, hybrid 3D image integration, etc. At step 1430, the processed and/or integrated data can be stored in a database (e.g., a robot learning database), displayed on a TV or a monitor inside or outside the portable enclosure. The computing system may analyze the detected signals and/or received/derived information and determine, or predict, the movements of the surgical and treatment instruments and the movements of the operator, such as, for example, a surgeon, and save a string of pictures of the movements mentioned above for further processing for other purposes, such as, for example, learning how a surgical robot operates.

The portable enclosure may have one or more video cameras or systems of video cameras placed inside or outside the enclosure in places selected to continuously monitor the surgical devices used by the operator and the operator hands, where the cameras are based on the intensity of the electromagnetic waves received by the cameras and the cameras may use visible light, infrared, ultraviolet, or terahertz electromagnetic waves, or combinations thereof and the cameras may send the detected signals and/or received/derived information to a computing system that combines signals/information from the TOF camera or system of cameras with the signals/information from the intensity-based cameras in order to compute the movements of the surgical instruments and/or the movements of the hands of the operator, such as, for example, a surgeon.

Figure 15:
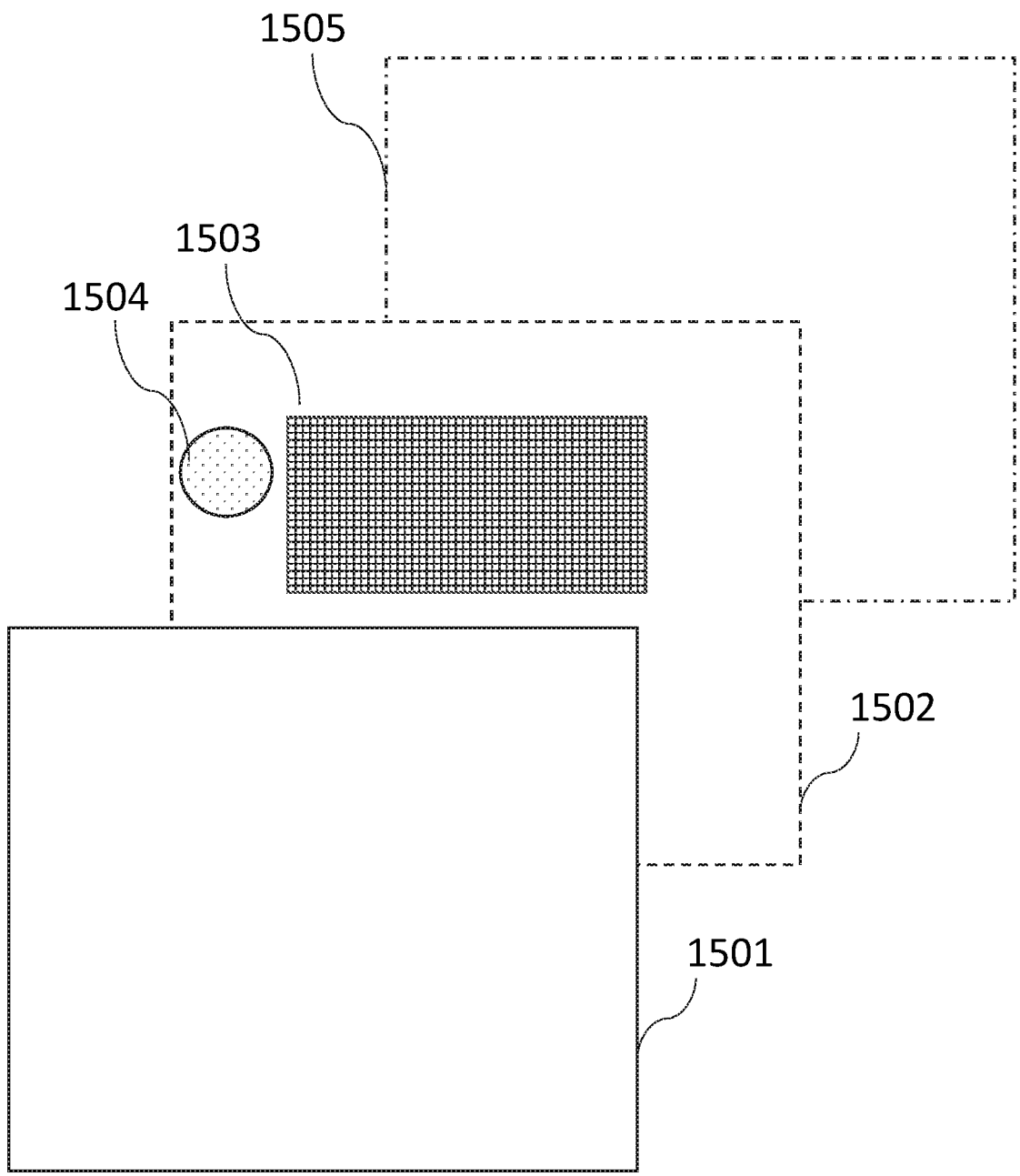
FIG. 15 shows an example of a portable surgical enclosure with a multi-layered wall including an electronics layer.

The portable enclosure may have a wall separating an internal sterile surgical environment from the outside user environment. The wall may comprise one or more layers. As shown in FIG. 15, an embodiment of such a portable enclosure may include an outer layer 1501, which may be a transparent flexible plastic, an inner layer 1502 which may include one or more displays 1503 and one or more sensors 1504. The display 1503 may be transparent or translucent when not in use. The display 1503 may not be transparent or translucent when not in use. While the display 1503 is on and in use, the display may or may not become less transparent or translucent in order to provide visual information on the surface of the device. The display 1503 may be an OLED, QLED, PMOLED, LCD, AMOLED, e-paper, or any other kind of display technology. The display 1503 may also be a touch-sensitive interface and include thin-film microprocessor or other electronics printed within layer 1502. Sensor 1504 may be an EKG lead which could touch the patient directly in the absence of a third layer 1505 or directly be embedded in the third layer 1505 in contact with a patient. The electronics may be powered through a battery or solar cell, for example PEDOT cells. The layer may include lighting elements, embedded cameras, and other sensors.

Sensors and other devices may also exist in an intermediate layer 1502 separate from the internal and external environments, where the internal environment is separated by a layer 1505 and the external environment faces layer 1501. This intermediate layer 1502 can house any sensing equipment or peripheral devices such as light emission devices, displays, touchscreens/interfaces, etc. Touch interfaces may include 5-Wire resistive, surface capacitive, projected capacitive, Surface Acoustic Wave (SAW), Infrared, among other implementations.

This printed electronics/intermediate layer 1502 can be built into the surgical enclosure wall. Additionally, this layer may be separate from the surgical enclosure, such that it exists in a sheet-like form that can be placed atop the periphery of the surgical enclosure. This process would be similar to laying a sheet on top of and against the walls of the surgical enclosure in a way that the device that was placed on the walls of the surgical enclosure augments the functionality of the enclosure. The addition of the sheet-like form could be of any size, either covering the wall in its entirety or only a portion. The augmenting layer can be made of a similar material of similar properties, or may be different, depending on desired functionality. The augmenting layer can be transparent or translucent to allow for vision through the layer. The augmenting layer can have multiple functions that include active devices or have passive effects. Additional functionality may include optical polarization, glare reduction, optical filtration of specific wavelengths, increased wall rigidity, increased wall durability, insulation, ventilation, humidity or moisture regulation, or temperature regulation.

Ports Structure of the Portable Surgical System

Figure 2:
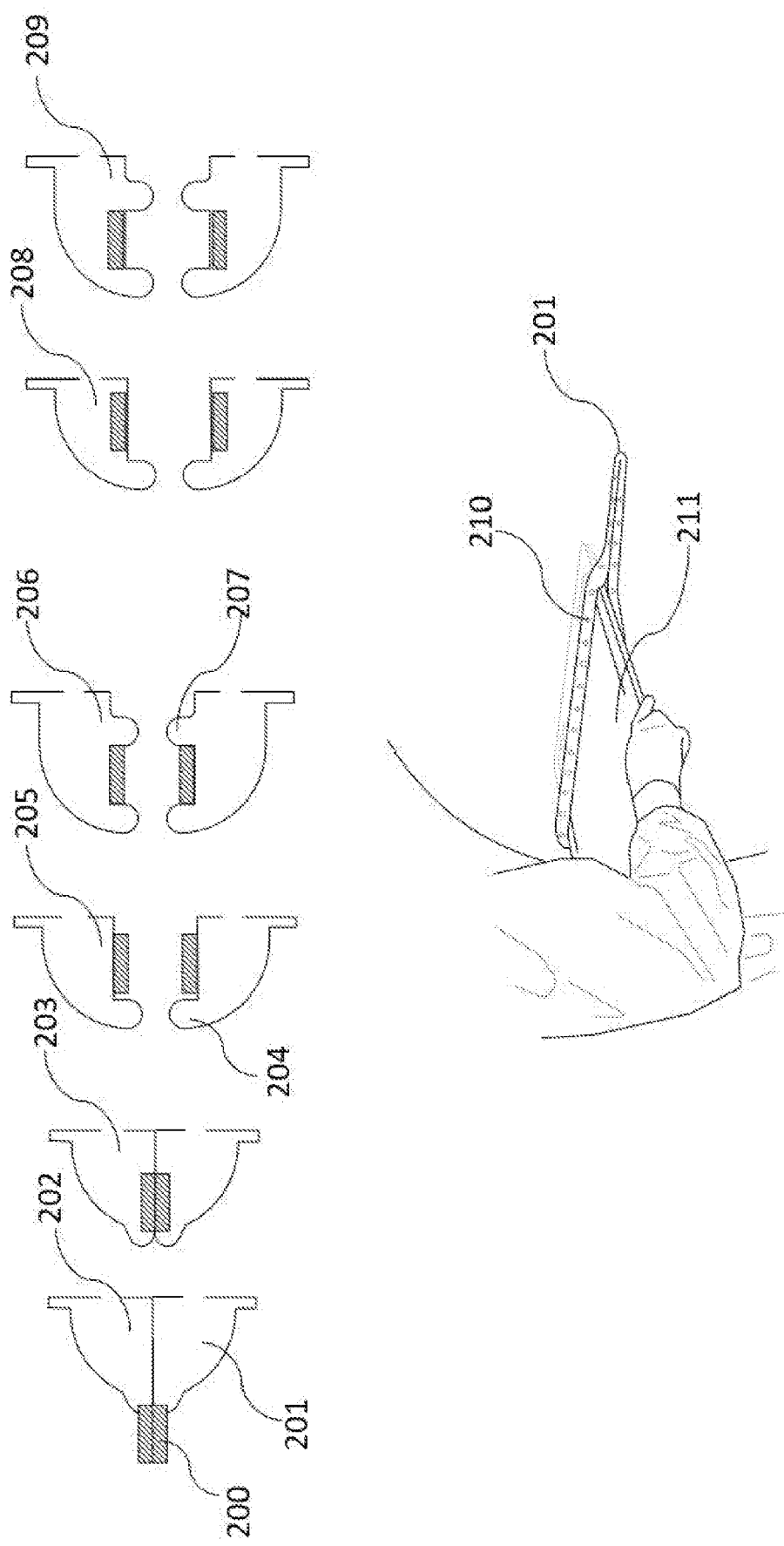
FIG. 2 is an example of a side view of different embodiments of a port of the surgical system, outlining different configurations used to maintain a barrier between the external and surgical environment.

FIG. 2 is an example of a side view of different embodiments of a port of the surgical system, outlining different configurations used to maintain a barrier between the external and surgical environment. The large port 105 in FIG. 1 is further explained in FIG. 2. Large port 105 can be configured from a number of embodiments. In FIG. 2, magnets (e.g., magnetic strip) 200 are used to establish two sides of port 201 so that they are attracted to each other. Air compartment (e.g., inflatable material, flexible inflatable tube) 202 is shared with the environment found in the sterile environment 101. This air compartment is designed with the intention to help seal any gaps that may exist between magnets 200. Cross-section of port 203 displays an embodiment with the magnets contained within the port. Cross-section 205 shows a different configuration of port 201, whereby the magnets are contained on the outside of the air compartment, with the air compartment 204 extending beyond the magnets to help establish a seal in front of the magnets. Cross-section 208 is similar to cross-section 205 with the magnets contained within the air compartment. Cross-section 206 is similar in that an extended air compartment 207 is established behind the magnets. Air compartments 204 and 206 may be used in combination or separately. Port 201 can be inflated through perforations 210 that are exposed to the internal environment of sterile enclosure 101. Element 211 is an example of a package that may be transferred between the external environment and internal sterile environment. As shown, the air compartments that are inflated by perforations 210 allow for a tighter seal around package 211, allowing for other similar packages or wires to be fed through port 201 and left to be partially exposed to the external environment and internal sterile environment with a reduced gapping between the two layers of port 201.

Figure 3:
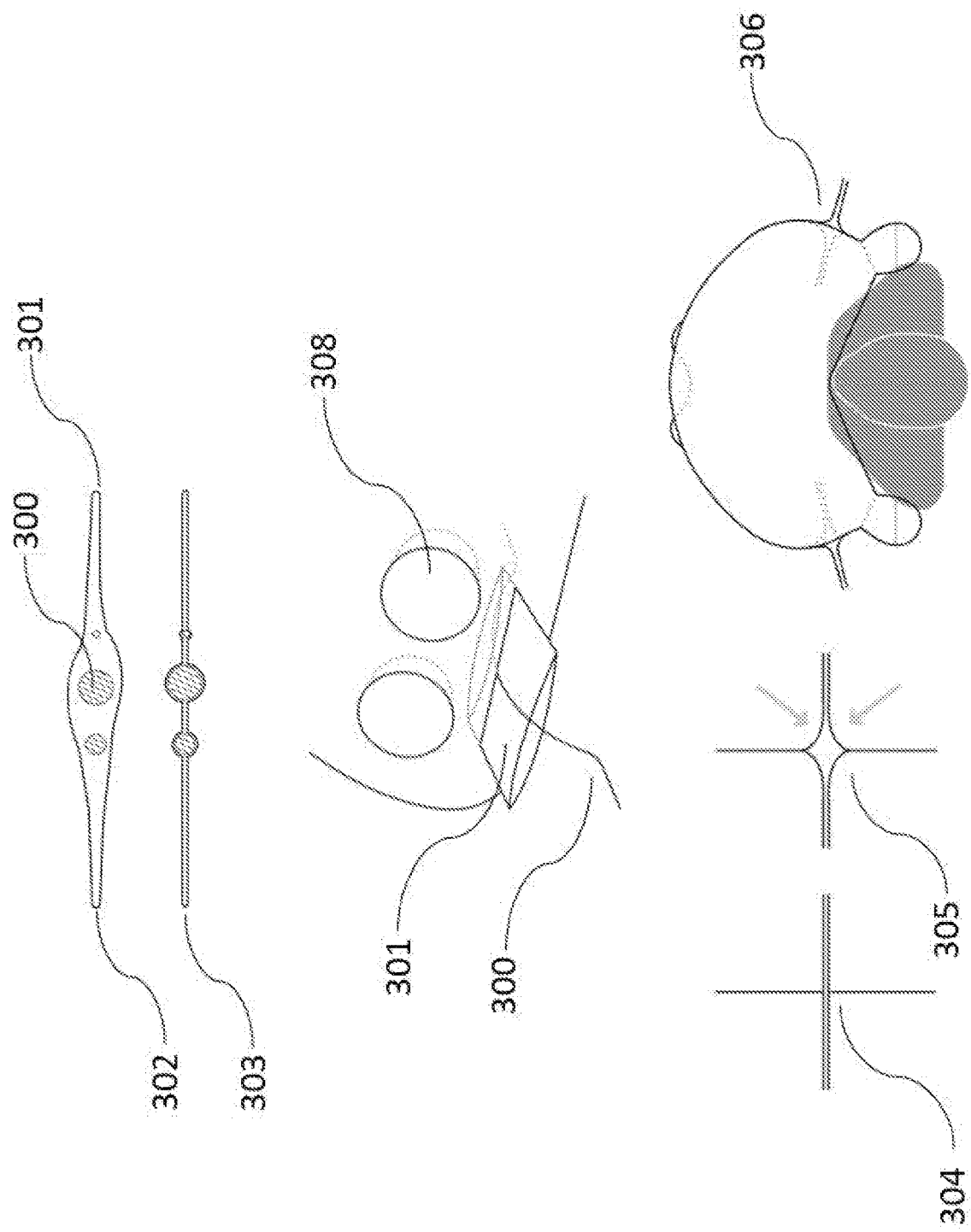
FIG. 3 is an example of a cross-sectional and overall view of a wire port that allows for wired instruments to traverse the barrier of the surgical system.

FIG. 3 is an example of a cross-sectional and overall view of a wire port that allows for wired instruments to traverse the barrier of the surgical system. Tool or wire port 301 has two configurations 302 and 303. Wires or tools 300 are inserted into the port 301, the port of which consists of two layers of material joined on the edges. Wire port configuration 302 displays the port in a condition whereby the internal sterile environment is not pressurized. Configuration 303 displays a condition whereby the port 301 is exposed to an internal sterile environment that is pressurized. The pressurization of internal sterile environment creates a pressure gradient between the internal sterile environment and external environment, establishing a closing of the material around wires and tools 300. Cross-section 304 describes how wire port 301 may traverse the barrier between the internal sterile environment and the external environment. Cross-section 305 illustrates the case in which the internal sterile environment is pressurized, with arrows pointing in the direction of forces being applied to the wire port that encourage it's forming around tools and wires placed within the port. Cross-section 306 shows how this may be implemented in the preferred embodiment. Additionally, in the preferred embodiment, these ports 301 may be placed directly under the sleeves 308.

Figure 4:
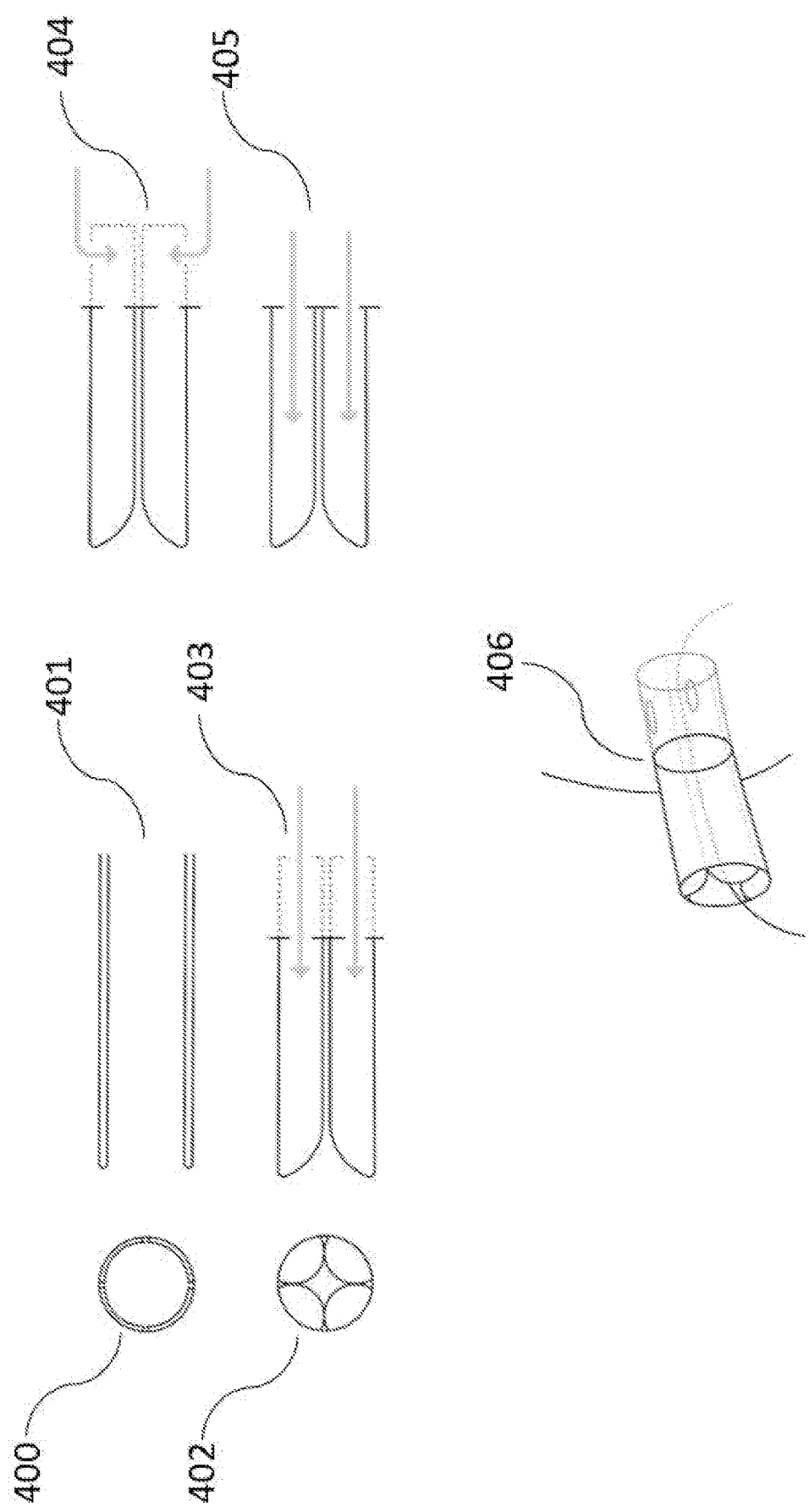
FIG. 4 is an example of a cross-sectional and overall view of an inflatable wire port that allows for wired instruments to traverse the barrier of the surgical system.

FIG. 4 is an example of a cross-sectional and overall view of an inflatable wire port that allows for wired instruments to traverse the barrier of the surgical system. In FIG. 4, a cylindrical inflatable port 400 provides a snug fit for a tool or wire entering the portable enclosure by the following process: increase of pressure in the inflatable walls 403 of the port 400 results in a closure of the inner walls 404 of the port 400 revealing a closed port position represented in a transversal section 405 and in cross section 402. The increase of pressure in the port's inflatable walls 403 results in a closed port 406 around an inserted cylindrical tool.

Figure 5:
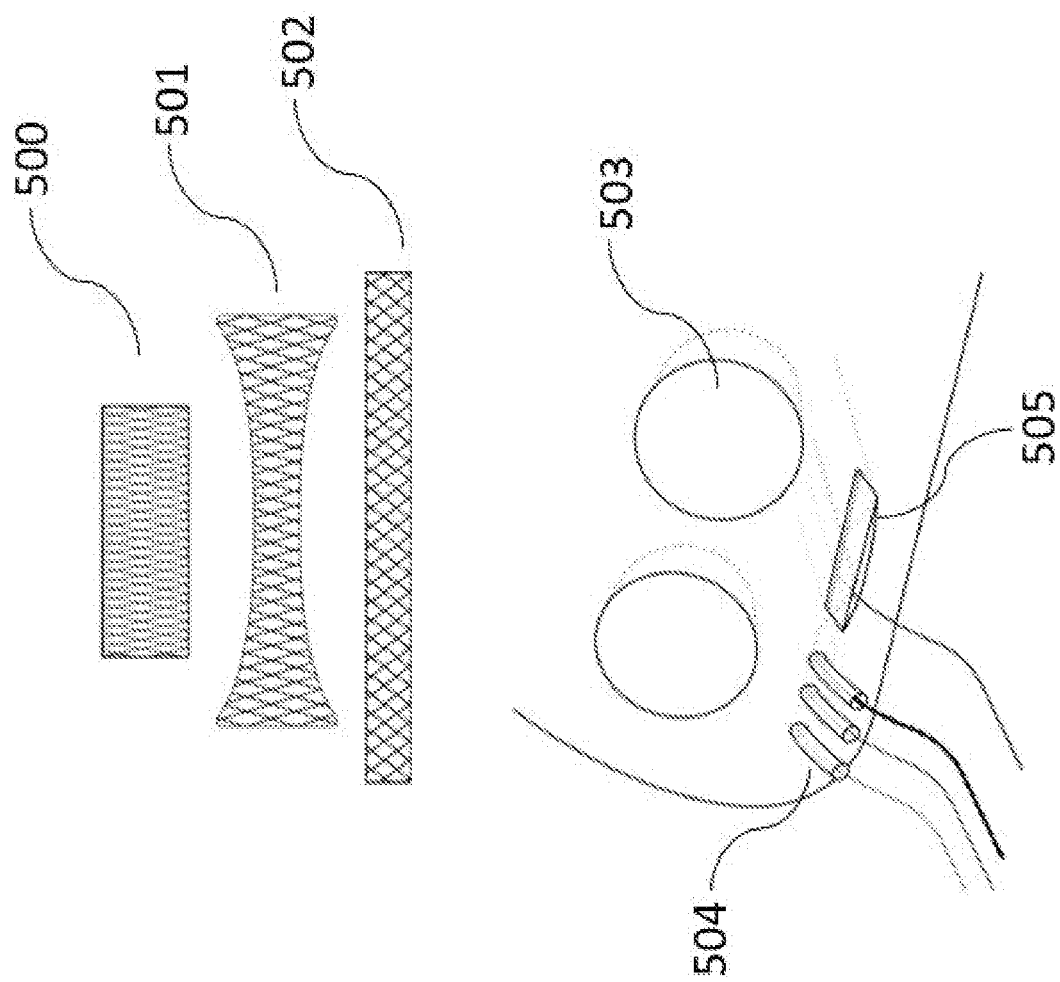
FIG. 5 is an example of a cross-sectional view of a woven wire port that constricts around the wire when lengthened, also containing a composite image of each of the wire ports in an example configuration.

FIG. 5 is an example of a cross-sectional view of a woven wire port that constricts around the wire when lengthened, also containing a composite image of each of the wire ports in an exemplary configuration. In FIG. 5, the port may include a helicoidal support structure 500 which compresses the inner tube 501 when extended 502. FIG. 5 shows an enclosure with multiple tools 504 entering inflatable ports 406 (shown in FIG. 4), a large magnetic orthostatic port 505 and surgical sleeves 503.

A portable surgical system may comprise one or more ports that are configured to enable a user to access the surgical environment without substantially changing volume or pressure of the portable enclosure. A portable enclosure may include two major types of ports. A first type of port on the enclosure may be arm ports, which may allow access to the inside of the enclosure by either provider arms or augmenting instrumentation taking the place of arms such as laparoscopes or robots. The number of arm ports may be at least about 1, 2, 3, 4, 5, 6, 7, 8, 9, 10, 15, 20 or greater. In some cases, the number of arm ports may be at most about 20, 15, 10, 9, 8, 7, 6, 5, 4, 3, 2, 1 or less. A second type of port on the enclosure may be a materials port, which may allow an instrument tray and instruments to be moved into the enclosure prior to the procedure. Additionally, the port may allow materials to be moved in and out of the enclosure throughout the surgical procedure (see PCT/US2017/042266). The port may be configured to enable a user to place an extremity within a surgical environment through a port that is designed to stretch over the extremity and hermetically seal at the point of entry over the extremity being inserted. The extremity may be any instrument, materials, or devices related to the surgical procedure. The size of stretched port may be at least about 1.1 times, 1.2 times, 1.5 times, 1.6 times, 1.8 times, 1.9 times, 2 times, 2.1 times, 2.2 times, 2.3 times, 2.4 times, 2.5 times, 2.6 times, 2.7 times, 2.8 times, 2.9 times, 3 times, or greater of the size of the non-stretched port. The size of stretched port may be at most about 3 times, 2.9 times, 2.8 times, 2.7 times, 2.6 times, 2.5 times, 2.4 times, 2.3 times, 2.2 times, 2.1 times, 2.0 times, 1.9 times, 1.8 times, 1.7 times, 1.6 times, 1.5 times, 1.4 times, or less of the size of the non-stretched port. The port may remain closed if not in use, since the airflow cannot be permitted to pass through.

A port may be configured to be perforated so that a user may be able to open and configure a size of the port to a desired size; have a port cover that may be removed so that the user may be able to open the port when desired; have a drawstring or adjustable diameter, so the user can change the size of the port to the desired size; or any combination thereof. For example, a portable enclosure may include both large ports and small ports. Small ports may be configured such that small items may be passed in or out of the enclosure without significant relative loss of enclosure volume or pressure. Large ports may permit the moving of large items like the instrument tray or neonates in and out of the enclosure. A port may also comprise a connector that splits a port in half, allowing it to act as a small port or large port. If a port has an adjustable diameter, the port may ensure that any user can have access to both a small port and a large port. In addition to episodic access for large items, ports can also provide ongoing access for lines, tubes, wires, and drains requiring access to external resources. A connector may be a zipper slider that slides over zipper teeth rows thereby adjusting a size of a port. Alternatively, it can be a material such as hook and loop fastener or magnets which provide rapidly reversible attachment.

One or more ports may comprise a magnetic strip, a hook-and-loop fastener, a plastic zipper, a flexible inflatable tube, a flexible plastic sheath, a helically wound braid, or any combination thereof. Hook-and-loop fasteners may comprise two components (e.g., two lineal fabric strips) which are attached (sewn or otherwise adhered) to the opposing surfaces to be fastened. A first component may comprise tiny hooks, and a second component may comprise smaller loops. Hooks may bind to the loops when two components are pressed together, and the two pieces fasten or bind temporarily.

A magnetic strip may be surrounded by an inflatable material that shares the positive pressure within the portable enclosure, inflating around the magnetic strip so that any gaps are filled by the inflated material. A magnetic strip may facilitate the closure of the port and an inflatable material may be brought closer together by the magnet, thereby creating a two-layered seal between both magnetic strips and inflated compartments.

A port with flexible inflatable tubes may remain inflated separately from the pressure generated from inside the portable enclosure. A port with flexible inflatable tubes may become inflated as the pressure within the portable enclosure increases.

A port may comprise a flexible plastic sheath extends on both sides of the wall of the portable enclosure and may be created by sealing two layers of material together along two opposing edges, effectively creating a channel to insert devices that will be sealed by the pressure gradient between the surrounding environment and the inside of the portable enclosure. A port with a helically wound braid may be made of a material that allows for the constriction of a port's circumference when the length of the braid is stretched and elongated. One or more ports may comprise magnetic strips surrounded by flexible inflatable tubes. Magnetic strips may be at least partially sealed when airflow goes through the flexible inflatable tubes.

A portable surgical system may comprise one or more wire tubes that are configured to hold one or more wires, cords, or cables. A given wire tube of the one or more wire tubes may be a collapsible tube configured to maintain a collapsed state when airflow through the collapsible tube is low such that the pressure exerted by the airflow is less than the radial inward pressure of the portable enclosure. In this situation, pressure exerted by the airflow may be at most about 90%, 80%, 70%, 60%, 50%, 40%, 30%, 20%, 10% or less of the radial inward pressure of the portable enclosure. In other embodiments, pressure exerted by the airflow may be at least about 10%, 20%, 30%, 40%, 50%, 60%, 70%, 80%, 90% or more of the radial inward pressure of the portable enclosure.

An open or closed state of a collapsible tube may serve as an indicator of airflow status of the portable enclosure. The shape of the collapsible tube (whether the tube is inflated or collapsed) may indicate airflow status. The airflow status may comprise flow rate, pressure, purity, or any combination thereof. When a collapsible tube is inflated, pressure of the airflow may be high in the portable enclosure. When a collapsible tube is collapsed, pressure of the airflow may be low in the portable enclosure.

One-Way Pressure Sensitive Valve

Figure 6:
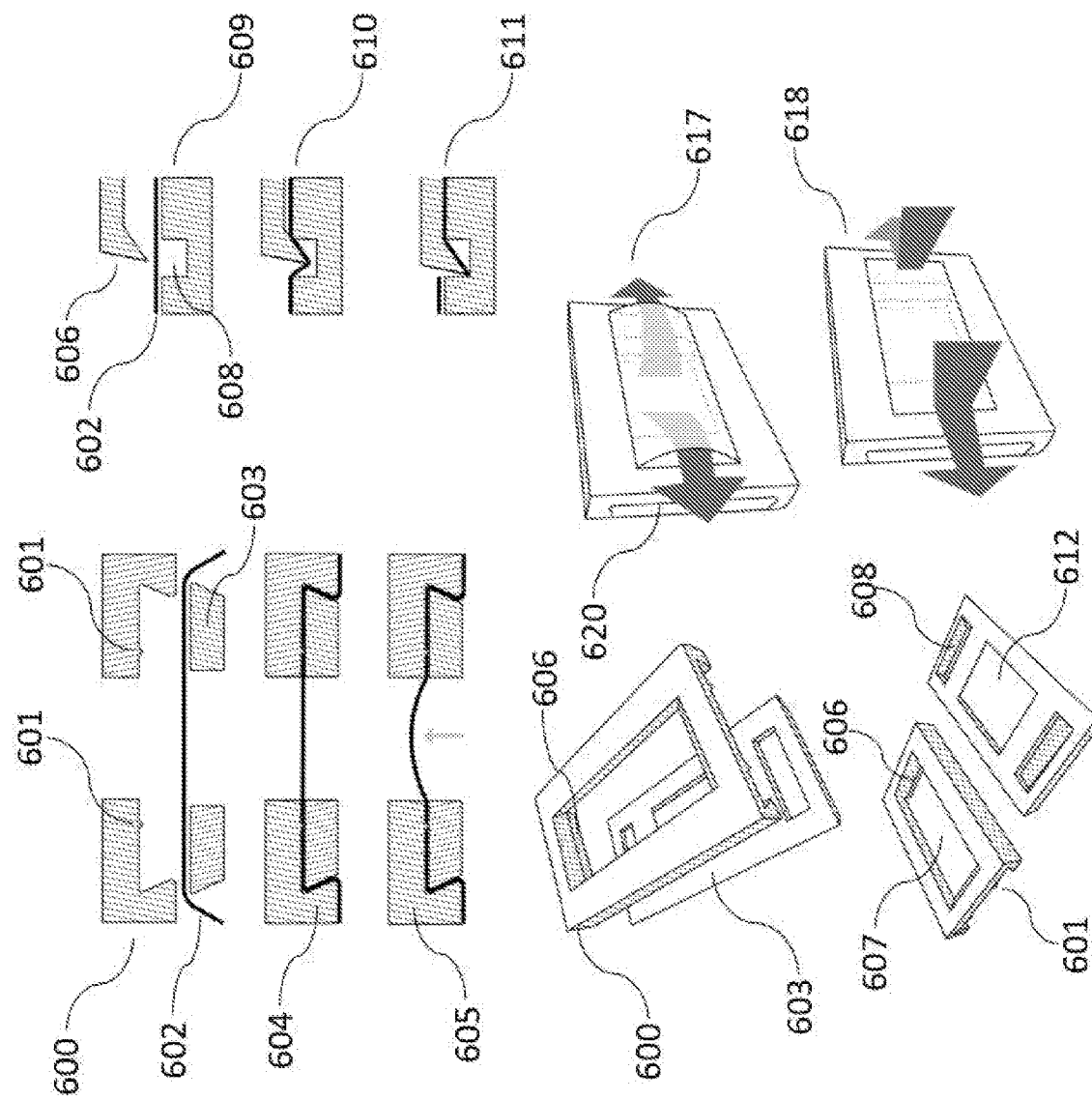
FIG. 6 is an example of a multi-view depiction of a one-way pressure sensitive valve outlining the components and functionality of the valve.

FIG. 6 is an example of a multi-view depiction of a one-way pressure sensitive valve outlining the components and functionality of the one-way pressure sensitive valve. FIG. 6 describes an example of the valve for the pressure-controlled release of gases (e.g., one-way pressure sensitive valve). As shown in FIG. 6, the one-way pressure sensitive valve comprises three parts, a top frame 600, a flexible material (e.g., membrane component) 602, and a bottom frame 603. The one-way pressure sensitive valve is designed to snap the top frame 600 and the bottom frame 603 together and sandwich the flexible material between the two frames 600 and 603 (e.g., frame components). Element 601 is a protrusion on top frame 600 designed to firmly hold the flexible material 602 against bottom frame 603. Protrusions 601 can be designed to change distance from each other, allowing for the modulation of tension within flexible material 602, and/or changing the pressure at which the one-way pressure sensitive valve opens. Configuration 604 displays the snapped together frames of the one-way pressure sensitive valve. Configuration 605 shows how an internal positive pressure of a sufficient difference to the external environment causes the flexible material 602 to distend. This distention allows for airflow out from the internal environment to the external environment as illustrated in 612. When the external pressure is equal to or greater than the internal pressure, the flexible material 602 would no longer be distended and will resist airflow from the external environment to the internal environment. This condition is shown in 613.

When snapping the frames 600 and 603 together, pointed or sharp element 606 may cut or penetrate flexible material 602. This transition between separate components and a fully assembled one-way pressure sensitive valve 614 is shown across 609, 610, and 611. When the two frames 600 and 603 are fully joined, pointed or sharp element 606 reaches into cavity 608, flexible material 602 is cut on two sides opposing to each other so that airflow can proceed through the one-way pressure sensitive valve 614 when the internal pressure becomes higher than the pressure of the external environment. Air is permitted to travel through holes 607 and 612 that are found in frames 600 and 612, respectively, when the internal pressure becomes higher than the pressure of the external environment.

A portable surgical system may comprise one or more outlets that comprise at least one one-way pressure sensitive valve. At least one one-way pressure sensitive valve may comprise a membrane component and a frame component. A membrane component may be part of the portable enclosure. A membrane component may be made of the same material as the portable enclosure. A membrane component may be made of different materials from the portable enclosure. A frame component may comprise a sharp edge.

A frame component may exist as two parts that are designed to snap together on opposing sides of the membrane. A shape of the outline of the two parts may be the same. A shape of the outline of the two parts may be different. A frame may be in any design, shape, and/or size. Examples of possible shapes or designs include but are not limited to: mathematical shapes (e.g., circular, triangular, square, rectangular, pentagonal, or hexagonal), two-dimensional geometric shapes, multi-dimensional geometric shapes, curves, polygons, polyhedral, polytopes, minimal surfaces, ruled surfaces, non-orientable surfaces, quadrics, pseudospherical surfaces, algebraic surfaces, miscellaneous surfaces, riemann surfaces, box-drawing characters, cuisenaire rods, geometric shapes, shapes with metaphorical names, symbols, unicode geometric shapes, other geometric shapes, partial shapes or combination of shapes thereof.

A membrane component may be cut by the sharp edge when the frame is clicked into place. A membrane may be cut prior to setting the valve. A membrane may be cut by the frame component prior setting the valve. A membrane may be cut after setting the valve.

A membrane component may be continuous with the enclosure to be pressurized and may be prepared such that the membrane component requires only the frame component to be functional.

A membrane component may be clamped in either variable tension or variable clamping distances with the intention to modulate the pressure at which the one-way valve produces exhaust from the portable enclosure. A clamping distance may be smaller than the length of the frame component. In some cases, a clamping distance may be at most about 90%, 80%, 70%, 60%, 50%, 40%, 30%, 20%, 10% or less of the length of the frame component. In other embodiments, a clamping distance may be at least about 10%, 20%, 30%, 40%, 50%, 60%, 70%, 80%, 90% or more of or less of the length of the frame component.

A one-way pressure sensitive valve may be covered by a removable film or covering that is to be removed after the setup of the portable enclosure, ensuring that no accidental backwards flow enters the portable enclosure before it is properly established. A film may be a thin film or a membrane and may be made of a polymer such as polyurethane, or any other medical-grade or food-grade plastics. A film may be latex free. A film may include antimicrobial, antiviral, germicidal, antipathogenic, and/or bactericidal properties. A film may or may not include silver, copper, titanium, other metals, formulas, or compounds. A film may also include any other antimicrobial formula, property, surface, or agent that is designed to help reduce concentrations of microbes, viruses, germs, pathogens, microorganisms, disease, or bacteria on the one-way sensitive valve. A film may have a thickness of at most 1000 µm, 500 µm, 400 µm, 300 µm, 200 µm, 100 µm, 50 µm, 40 µm, 30 µm, 20 µm, 10 µm or less. In some cases, a film may have a thickness of at least 10 µm, 20 µm, 30 µm, 40 µm, 50 µm, 100 µm, 150 µm, 200 µm, 300 µm, 400 µm, 500 µm, 1000 µm or more.

A one-way pressure sensitive valve may include biologically acceptable materials suitable for medical applications, depending on the particular application and/or preference of a medical practitioner. For example, the materials may comprise cellophane, vinyl, acetate, polyethylene acrylic, butyl rubber, ethylene-vinyl acetate, natural rubber, a nitrile, silicone rubber, a styrene block copolymer, a vinyl ether, or a tackifier. Antimicrobial and/or antiseptic materials may include but are not limited to: sodium bicarbonate; hydrogen peroxide; benzalkonium chloride; chlorohexidine; hexachlorophene; iodine compounds; and combinations thereof. In some embodiments, the antimicrobial and/or antiseptic materials may not include alcohols (such as ethanol, 1-propanol and 2-propanol/isopropanol or mixtures of these alcohols), since solvents/alcohols may promote the airborne transmission of certain types of micro-organisms, and certain type of microbes may be resistant to alcohols. Antimicrobial materials can further include but are not limited to: beta-lactam antibiotics (such as penicillin, cephalosporin); protein synthesis inhibitors (such as aminoglycosides, macrolides, tetracycline, chloramphenicol, polypeptides); sulphonamides; cotrimoxazole; quinolones; anti-viral agents; anti-fungal agents; anti-cancer drugs; anti-malarial drugs; anti-tuberculosis drugs; anti-leprotic drugs; anti-protozoal drugs or combinations thereof.

At least one one-way pressure sensitive valve may release airflow from a surgical environment to a user environment when the pressure of the internal environment is sufficiently greater than the user environment. For at least one one-way pressure sensitive valve to release airflow from a surgical environment to a user environment, pressure of an internal environment may be at least about 1.1 times, 1.2 times, 1.5 times, 1.6 times, 1.8 times, 1.9 times, 2 times, 2.1 times, 2.2 times, 2.3 times, 2.4 times, 2.5 times, 2.6 times, 2.7 times, 2.8 times, 2.9 times, 3 times, or greater of the pressure in the user environment. For at least one one-way pressure sensitive valve to release airflow from the surgical environment to the user environment, pressure of an internal environment may be at most about 3 times, 2.9 times, 2.8 times, 2.7 times, 2.6 times, 2.5 times, 2.4 times, 2.3 times, 2.2 times, 2.1 times, 2.0 times, 1.9 times, 1.8 times, 1.7 times, 1.6 times, 1.5 times, 1.4 times, or less of the pressure in the user environment.

Methods of Using the Portable Surgical System Comprising an Airflow Device

A portable surgical system can comprise a surgical enclosure, an airflow device, a battery pack to power up the airflow device, and a plurality of supports (e.g., metal supports). FIGS. 8A-8E shows various components of an example portable surgical system, including for example an airflow device, a battery pack to power the airflow device, and a plurality of metal supports.

FIG. 8A shows the right side perspective view of an airflow device 810. FIG. 8B depicts the left side perspective view of the airflow device 810. The airflow device 810 can comprise a body 812 within which houses an air compressor (not shown), an open end (e.g., an air flow adaptor) 814 configured to connect to an airflow tube of a portable enclosure (not shown), a power cable adaptor 816, a power cable 818 plugged into the power cable adaptor 816, and a control knob 820 configured to control the operation of the airflow device.

FIG. 8C shows the right side perspective view of a battery pack 830. FIG. 8D shows the top view of the battery pack 830. The battery pact 830 can comprises one or more batteries (not shown), a power cable adaptor 832, a power button 834 on the top side, and a screen 836 on the top side.

FIG. 8E shows four short supports and a long support. Other combination of supports with different dimensions, with different numbers, or from different compositions (e.g., metal-based or polymer-based) may be possible.

FIGS. 9A-9C show an enclosure when packed or when deployed. FIG. 9A shows a perspective view of an enclosure 900 when it is packed. The packed enclosure 900 may be configured to fit into a backpack or other containers that are portable. FIG. 9B shows the top view of an unpacked enclosure 900A. FIG. 9C shows the bottom view of the unpacked enclosure 900A. The unpacked enclosure 900A comprises a barrier 912, one or more sleeves 914, tool entry port 916, air tube 918, and incise drape 920.

FIGS. 10A-10C show the setup of an enclosure 1000. FIG. A shows the enclosure 1000 is placed on the body of a subject 1050. The subject 1050 has a surgery site 1052. The enclosure 1000 is shown in FIG. 10A to change from a packed configuration to an unpacked configuration over body of the subject 1050 with the intent to cover the surgery site when fully unpacked. The unpacking process may comprise: unwrap and roll the enclosure 1000 over the subject 1050 such that the incise drape 1020 lands at the surgery site 1052 (i.e., the intended location of the surgery).

FIG. 10 B shows that an adhesive layer 1014 on the back of the incise drape 1020 can be peeled off such that the exposed bottom face of the incise drape 1020 can be placed on the affected area around the surgery site 1052 on the subject 1050.

FIG. 10C shows a schematic view of the unpacked enclosure 1000 over the body of the subject 1050. The unpacked enclosure 100 is not inflated yet. The unpacked enclosure comprises a barrier 1012, one or more sleeves 1014, air tube 1018, and incise drape 1020 over the surgery site 1052.

Figure 11A:
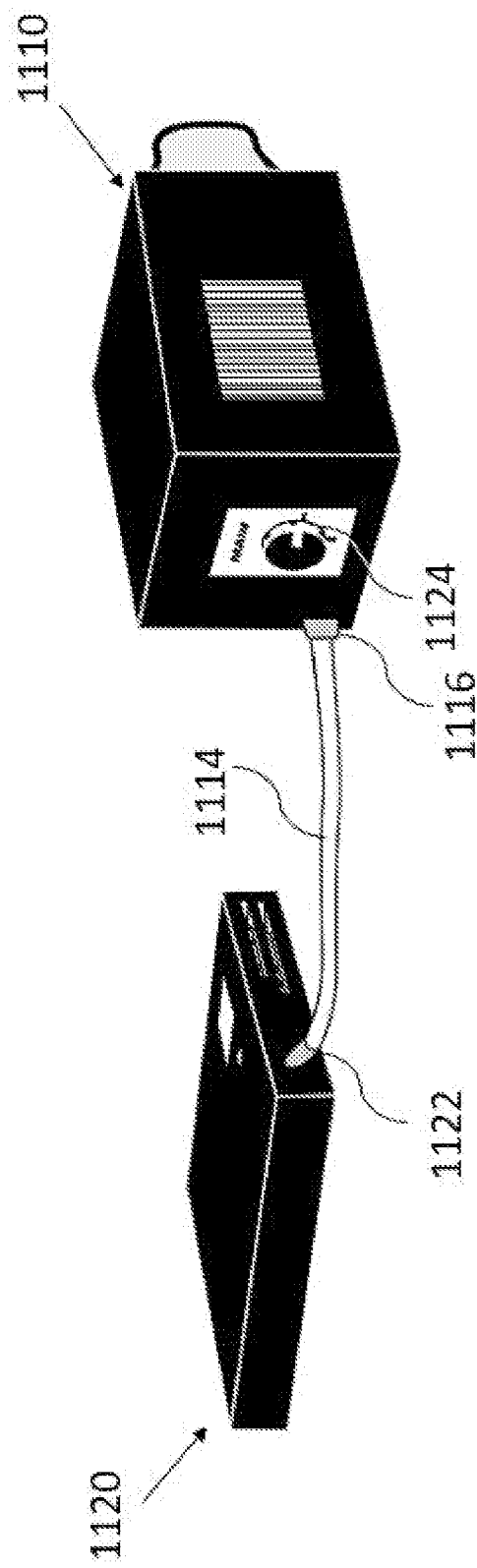
FIG. 11A shows a perspective view of a power source (e.g., a battery pack) connected with a portable environment control system (e.g., an airflow device) via a power cable.
Figure 11B:
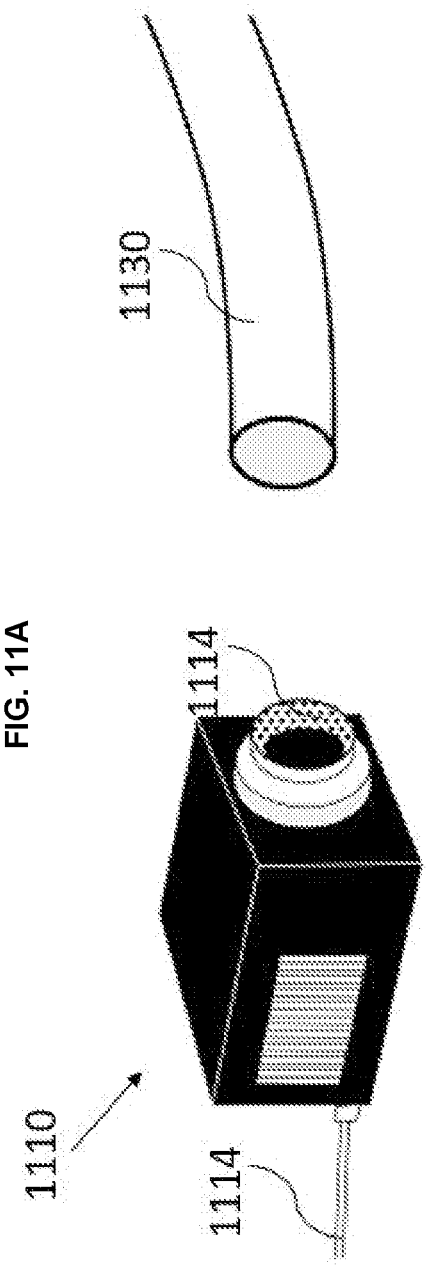
FIG. 11B shows a partial perspective view of connecting the portable surgical system the environment control system (e.g., an airflow device)

As shown in FIGS. 11A-11B, an unpacked enclosure can then be inflated. For example, an airflow device 1110 and a battery pack 1120 can be used to inflate an enclosure (not shown) through an airflow tube 1130 on the enclosure. As shown in FIG. 11A, first, connect the airflow device 1110 with the battery pack 1120 via a power cable 1114 connecting a power cable adaptor 1116 on the airflow device 1110 and a power cable adaptor 1122 on the battery pack 1120. At this stage, the battery pack 1120 may not be turned on. As shown in FIG. 11B, second, attach the airflow tube 1130 to an open end (e.g., an air flow adaptor) 1118 such that the airflow device 1110, when powered by the battery pack 1120, is configured to inflate the enclosure by pumping air through the airflow tube 1130.

Subsequently, press the power button of the battery pack 1120 to engage the battery pack 1120 to provide power to the airflow device 1110. After the battery pack 1120 is engaged, activate the airflow device 1110 by using the control knob 1124 on the airflow device. The airflow rate of the air pumped into the enclosure via the airflow tube 1130 can be adjusted by the control knob 1124. Consequently, the enclosure is inflated and a positive pressure (e.g., higher pressure) can be maintain inside the enclosure relative to the pressure of the environment outside the enclosure.

FIG. 12A shows an example of inflated portable surgical system 1200 on a subject 1250. The portable surgical system 1200 comprises a barrier 1202, supports 1204 configured to suspend the barrier 1202 over the subject 1250, incise drape 1206, airflow tube 1208 configured to provide a positive pressure inside the barrier 1202, one or more sleeves 1210 for an operator to reach into the barrier 1202 and operate on the subject 1250, electronics layer 1212 embedded with the barrier 1202, one or more light source/monitor/sensor/detector 1214 configured to record or monitor the operation or movements of any objects inside or in the vicinity of the barrier 1202, an airflow device 1220 connected to the airflow tube 1208 and configured to provide sterile air, a battery pack 1230 configured to provide power to the airflow device 1220, and a power cable 1222 connecting the battery pack 1230 with the airflow device 1220. Supports 1204 can be metal or polymer-based support rods to secure the barrier 1202. FIG. 12B shows a schematic view of the sleeve 1210. Sleeve 1210 comprises a perforated tab 1216 on the external side of the sleeve and an open cuff 1224 on the internal side of the sleeve. For an operator to safely enter the sterile space of the portable surgical system 1200, he can tear off the perforated tab 1216, reach into the sleeve 1210 from the opening 1218 and through the open cuff 1224. The control knob on the airflow device can be adjusted to control the flow rate of the air going into the sterile space inside the barrier 1202 and keep the barrier inflated for the operation to be conducted.

Turning now to tool entry, FIGS. 13A-13B demonstrates an example method of transferring tool safely into the sterile space of a portable surgical system 1300. FIG. 13A shows a partial top view of the portable surgical system 1300. The portable surgical system 1300 comprises a barrier 1302, large tool port 1304, incise drape 1306, and one or more sleeves 1310 for an operator to reach into the barrier 1302. FIG. 13B shows a perspective view of the portable surgical system 1300 whose large tool port 1304 is open. The portable surgical system 1300 comprises a barrier 1302, large tool port 1304 (opened to provide an opening 1316 for tools to enter), incise drape 1306, one or more sleeves 1310 for an operator to reach into the barrier 1302, electronics layer 1312 embedded with the barrier 1302, one or more light source/monitor/sensor/detector 1314 configured to record or monitor the operation or movements of any objects inside or in the vicinity of the barrier 1302. Accordingly, to bring tools inside the portable surgical system 1300, the large tool port 1304 can be opened (e.g., by pulling apart the magnetic bars on the opposite sides of the opening 1316). Once the opening 1316 is large enough for the tools to enter, enter tools into the sterile space inside the barrier through the opening 1316. After the tools have been safely entered, close the opening 1316 (e.g., by snapping the magnetic bars on the opposite sides of the opening 1316 together).

Methods of Training Surgical Robots

In an aspect, a method of training a surgery robot, simulation, or providing reference material for educational purposes may comprise providing a portable surgical system described elsewhere herein; receiving data collected from one or more sensors that are disposed in or around a portable surgical system and comprise at least one motion sensor for detecting a movement of a surgical instrument, a medical professional, a surgery robot, or any combination thereof generating procedure information based on data, wherein the procedure information comprises instructions for performing a surgical procedure; and training a control algorithm for controlling a surgery robot using datasets, wherein the datasets are generated using the procedure information.

Data may further comprise structured data, time-series data, unstructured data, and relational data. Unstructured data may comprise audio data, image data, video, mechanical data, electrical data, chemical data, and any combination thereof, for use in accurately simulating or training robotics or simulations. Time-series data may comprise data from one or more of a smart meter, a smart appliance, a smart device, a monitoring system, a telemetry device, or a sensor. Relational data comprises data from a customer system, an enterprise system, an operational system, a website, web accessible application program interface (API), or any combination thereof. This may be done by a user through any method of inputting files or other data formats into software or systems. Data may be stored in a database. The database is described elsewhere herein.

Instructions may comprise information related to a surgical procedure. A surgical procedure may comprise, but are not limited to, appendectomy, breast biopsy, carotid endarterectomy, cataract surgery, cesarean section, cholecystectomy, coronary artery bypass, debridement of wound, dilation and curettage, free skin graft, hemorrhoidectomy, hysterectomy, hysteroscopy, inguinal hernia repairs, low back pain surgery, mastectomy, partial mastectomy, modified radical mastectomy surgery, radical mastectomy, spinal disk fusion, spinal related surgeries, amputations, fracture fixations (internal and external), joint repair and replacement, partial colectomy, prostatectomy, releasing of peritoneal adhesions, tonsillectomy, or any combination thereof. Information related to a surgical procedure may comprise, but are not limited to, preparation for a surgery, performing tests before a surgery, how to perform a surgery, a recovery process, or any combination thereof.

A method may comprise visual analysis of a surgical environment through infrared, visible light, ultraviolet, x-ray. A method may comprise audio analysis of a surgical environment through microphones and visual vibration analysis. A method may comprise mechanical, electrical, and chemical analysis of a surgical environment using sensors described elsewhere herein. A visual, audio, mechanical, electrical, and/or chemical analysis may be performed at the same time when a surgical procedure is performed. A visual, audio, mechanical, electrical, and/or chemical analysis may be performed when a surgical procedure is not performed. A visual, audio, mechanical, electrical, and/or chemical analysis of a surgical environment may provide data or information related to temperature, pressure, humidity, luminance, heart rate, breathing rate, blood pressure, blood oxygen saturation, electrocardiography, electromyography, skin conductance, airflow, air quality, internal and external gas composition, a chemical composition of a surgical environment, or any combination thereof.

Data may be uploaded to a cloud-based database. Datasets may be uploaded to a cloud-based database. Cloud-based database and associated software may be used for archiving electronic data, sharing electronic data, analyzing electronic data, or any combination thereof. Optical data or datasets generated locally may be uploaded to a cloud-based database, from which it may be accessed and used to train other machine learning-based detection systems at the same site or a different site. Sensor device and system test results generated locally may be uploaded to a cloud-based database and used to update training data set in real time for continuous improvement of sensor device and detection system test performance.

Datasets may be processed with the intention for training machine learning, artificial intelligence, or other statistically based algorithms. A machine learning algorithm (or software module) may utilize one or more neural networks. A trained algorithm (e.g., control algorithm) may comprise one or more neural networks. A neural network may be a type of computational system that can learn the relationships between an input data set and a target data set. A neural network may be a software representation of a human neural system (e.g. cognitive system), intended to capture "learning" and "generalization" abilities as used by a human. A neural network may comprise a series of layers termed "neurons" or "nodes." A neural network may comprise an input layer, to which data is presented; one or more internal, and/or "hidden," layers; and an output layer. A neuron may be connected to neurons in other layers via connections that have weights, which are parameters that control the strength of a connection. The number of neurons in each layer may be related to the complexity of a problem to be solved. The minimum number of neurons required in a layer may be determined by the problem complexity, and the maximum number may be limited by the ability of a neural network to generalize. Input neurons may receive data being presented and then transmit that data to the first hidden layer through connections' weights, which are modified during training. The node may sum up the products of all pairs of inputs and their associated weights. The weighted sum may be offset with a bias. The output of a node or neuron may be gated using a threshold or activation function. An activation function may be a linear or non-linear function. An activation function may be, for example, a rectified linear unit (ReLU) activation function, a Leaky ReLu activation function, or other function such as a saturating hyperbolic tangent, identity, binary step, logistic, arcTan, softsign, parameteric rectified linear unit, exponential linear unit, softPlus, bent identity, softExponential, Sinusoid, Sinc, Gaussian, or sigmoid function, or any combination thereof.

A first hidden layer may process data and transmit its result to the next layer through a second set of weighted connections. Each subsequent layer may "pool" results from previous layers into more complex relationships. Neural networks may be programmed by training them with a known sample set (data collected from one or more sensors) and allowing them to modify themselves during (and after) training so as to provide a desired output such as an output value. A trained algorithm may comprise convolutional neural networks, recurrent neural networks, dilated convolutional neural networks, fully connected neural networks, deep generative models, and Boltzmann machines.

Weighting factors, bias values, and threshold values, or other computational parameters of a neural network, may be "taught" or "learned" in a training phase using one or more sets of training data. For example, parameters may be trained using input data from a training data set and a gradient descent or backward propagation method so that output value(s) that a neural network computes are consistent with examples included in training data set.

The number of nodes used in an input layer of a neural network may be at least about 10, 50, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000 or greater. In other instances, the number of node used in an input layer may be at most about 100,000, 90,000, 80,000, 70,000, 60,000, 50,000, 40,000, 30,000, 20,000, 10,000, 9000, 8000, 7000, 6000, 5000, 4000, 3000, 2000, 1000, 900, 800, 700, 600, 500, 400, 300, 200, 100, 50, or 10 or smaller. In some instance, the total number of layers used in a neural network (including input and output layers) may be at least about 3, 4, 5, 10, 15, 20, or greater. In other instances, the total number of layers may be at most about 20, 15, 10, 5, 4, 3 or less.

In some instances, the total number of learnable or trainable parameters, e.g., weighting factors, biases, or threshold values, used in a neural network may be at least about 10, 50, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000 or greater. In other instances, the number of learnable parameters may be at most about 100,000, 90,000, 80,000, 70,000, 60,000, 50,000, 40,000, 30,000, 20,000, 10,000, 9000, 8000, 7000, 6000, 5000, 4000, 3000, 2000, 1000, 900, 800, 700, 600, 500, 400, 300, 200, 100, 50, or 10 or smaller.

A neural network may comprise a convolutional neural network. A convolutional neural network may comprise one or more convolutional layers, dilated layers or fully connected layers. The number of convolutional layers may be between 1-10 and dilated layers between 0-10. The total number of convolutional layers (including input and output layers) may be at least about 1, 2, 3, 4, 5, 10, 15, 20, or greater, and the total number of dilated layers may be at least about 1, 2, 3, 4, 5, 10, 15, 20, or greater. The total number of convolutional layers may be at most about 20, 15, 10, 5, 4, 3 or less, and the total number of dilated layers may be at most about 20, 15, 10, 5, 4, 3 or less. In some embodiments, the number of convolutional layers is between 1-10 and fully connected layers between 0-10. The total number of convolutional layers (including input and output layers) may be at least about 1, 2, 3, 4, 5, 10, 15, 20, or greater, and the total number of fully connected layers may be at least about 1, 2, 3, 4, 5, 10, 15, 20, or greater. The total number of convolutional layers may be at most about 20, 15, 10, 5, 4, 3 or less, and the total number of fully connected layers may be at most about 20, 15, 10, 5, 4, 3 or less.

A convolutional neural network (CNN) may be deep and feed-forward artificial neural networks. A CNN may be applicable to analyzing visual imagery. A CNN may comprise an input, an output layer, and multiple hidden layers. Hidden layers of a CNN may comprise convolutional layers, pooling layers, fully connected layers and normalization layers. Layers may be organized in 3 dimensions: width, height and depth.

Convolutional layers may apply a convolution operation to an input and pass results of a convolution operation to a next layer. For processing images, a convolution operation may reduce the number of free parameters, allowing a network to be deeper with fewer parameters. In a convolutional layer, neurons may receive input from only a restricted subarea of a previous layer. Convolutional layer's parameters may comprise a set of learnable filters (or kernels).

Learnable filters may have a small receptive field and extend through the full depth of an input volume. During a forward pass, each filter may be convolved across the width and height of an input volume, compute a dot product between entries of a filter and an input, and produce a 2-dimensional activation map of that filter. As a result, a network may learn filters that activate when it detects some specific type of feature at some spatial position in an input.

Pooling layers may comprise global pooling layers. Global pooling layers may combine outputs of neuron clusters at one layer into a single neuron in the next layer. For example, max pooling layers may use the maximum value from each of a cluster of neurons at a prior layer; and average pooling layers may use an average value from each of a cluster of neurons at the prior layer. Fully connected layers may connect every neuron in one layer to every neuron in another layer. In a fully-connected layer, each neuron may receive input from every element of a previous layer. A normalization layer may be a batch normalization layer. A batch normalization layer may improve a performance and stability of neural networks. A batch normalization layer may provide any layer in a neural network with inputs that are zero mean/unit variance. Advantages of using batch normalization layer may include faster trained networks, higher learning rates, easier to initialize weights, more activation functions viable, and simpler process of creating deep networks.

A neural network may comprise a recurrent neural network. A recurrent neural network may be configured to receive sequential data as an input, such as consecutive data inputs, and a recurrent neural network software module may update an internal state at every time step. A recurrent neural network can use internal state (memory) to process sequences of inputs. A recurrent neural network may be applicable to tasks such as handwriting recognition or speech recognition, next word prediction, music composition, image captioning, time series anomaly detection, machine translation, scene labeling, and stock market prediction. A recurrent neural network may comprise fully recurrent neural network, independently recurrent neural network, Elman networks, Jordan networks, Echo state, neural history compressor, long short-term memory, gated recurrent unit, multiple timescales model, neural Turing machines, differentiable neural computer, neural network pushdown automata, or any combination thereof.

A trained algorithm may comprise a supervised or unsupervised learning method such as, for example, SVM, random forests, clustering algorithm (or software module), gradient boosting, logistic regression, and/or decision trees. Supervised learning algorithms may be algorithms that rely on the use of a set of labeled, paired training data examples to infer the relationship between an input data and output data. Unsupervised learning algorithms may be algorithms used to draw inferences from training data sets to output data. Unsupervised learning algorithm may comprise cluster analysis, which may be used for exploratory data analysis to find hidden patterns or groupings in process data. One example of unsupervised learning method may comprise principal component analysis. Principal component analysis may comprise reducing the dimensionality of one or more variables. The dimensionality of a given variable may be at least 1, 5, 10, 50, 100, 200, 300, 400, 500, 600, 700, 800, 900, 1000, 1100, 1200 1300, 1400, 1500, 1600, 1700, 1800, or greater. The dimensionality of a given variable may be at most 1800, 1600, 1500, 1400, 1300, 1200, 1100, 1000, 900, 800, 700, 600, 500, 400, 300, 200, 100, 50, 10 or less.

A statistical based algorithm may be obtained through statistical techniques. In some embodiments, statistical techniques may comprise linear regression, classification, resampling methods, subset selection, shrinkage, dimension reduction, nonlinear models, tree-based methods, support vector machines, unsupervised learning, or any combination thereof.

A linear regression may be a method to predict a target variable by fitting the best linear relationship between a dependent and independent variable. The best fit may mean that the sum of all distances between a shape and actual observations at each point is the least. Linear regression may comprise simple linear regression and multiple linear regression. A simple linear regression may use a single independent variable to predict a dependent variable. A multiple linear regression may use more than one independent variable to predict a dependent variable by fitting a best linear relationship.

A classification may be a data mining technique that assigns categories to a collection of data in order to achieve accurate predictions and analysis. Classification techniques may comprise logistic regression and discriminant analysis. Logistic Regression may be used when a dependent variable is dichotomous (binary). Logistic regression may be used to discover and describe a relationship between one dependent binary variable and one or more nominal, ordinal, interval or ratio-level independent variables. A resampling may be a method comprising drawing repeated samples from original data samples. A resampling may not involve a utilization of a generic distribution tables in order to compute approximate probability values. A resampling may generate a unique sampling distribution on a basis of an actual data. In some embodiments, a resampling may use experimental methods, rather than analytical methods, to generate a unique sampling distribution. Resampling techniques may comprise bootstrapping and cross-validation. Bootstrapping may be performed by sampling with replacement from original data and take "not chosen" data points as test cases. Cross validation may be performed by split training data into a plurality of parts.

A subset selection may identify a subset of predictors related to a response. A subset selection may comprise best-subset selection, forward stepwise selection, backward stepwise selection, hybrid method, or any combination thereof. In some embodiments, shrinkage fits a model involving all predictors, but estimated coefficients are shrunken towards zero relative to the least squares estimates. This shrinkage may reduce variance. A shrinkage may comprise ridge regression and a lasso. A dimension reduction may reduce a problem of estimating n+1 coefficients to a simple problem of m+1 coefficients, where n<m. It may be attained by computing n different linear combinations, or projections, of variables. Then these n projections are used as predictors to fit a linear regression model by least squares. Dimension reduction may comprise principal component regression and partial least squares. A principal component regression may be used to derive a low-dimensional set of features from a large set of variables. A principal component used in a principal component regression may capture the most variance in data using linear combinations of data in subsequently orthogonal directions. The partial least squares may be a supervised alternative to principal component regression because partial least squares may make use of a response variable in order to identify new features.

A nonlinear regression may be a form of regression analysis in which observational data are modeled by a function which is a nonlinear combination of model parameters and depends on one or more independent variables. A nonlinear regression may comprise step function, piecewise function, spline, generalized additive model, or any combination thereof.

Tree-based methods may be used for both regression and classification problems. Regression and classification problems may involve stratifying or segmenting the predictor space into a number of simple regions. Tree-based methods may comprise bagging, boosting, random forest, or any combination thereof. Bagging may decrease a variance of prediction by generating additional data for training from original dataset using combinations with repetitions to produce multistep of the same carnality/size as original data. Boosting may calculate an output using several different models and then average a result using a weighted average approach. A random forest algorithm may draw random bootstrap samples of a training set. Support vector machines may be classification techniques. Support vector machines may comprise finding a hyperplane that best separates two classes of points with the maximum margin. Support vector machines may be constrained optimization problem where a margin is maximized subject to a constraint that it perfectly classifies data.

Unsupervised methods may be methods to draw inferences from datasets comprising input data without labeled responses. Unsupervised methods may comprise clustering, principal component analysis, k-Mean clustering, hierarchical clustering, or any combination thereof.

Method of Manufacturing a Portable Surgical System

A portable surgical system or a portable enclosure may be formed by using one or more manufacturing techniques. One or more manufacturing techniques may comprise, but are not limited to, casting, imaging, coating, molding, forming, machining, joining, welding, RF welding, heat welding, chemical welding, additive manufacturing processes such as 3D printing, or any combination thereof.

A casting may comprise die casting, centrifugal casting, continuous casting, evaporative-pattern casting, resin casting, shell molding, vacuum molding, or any combination thereof. An imaging and coating may comprise laser engraving, inkjet printing, chemical vapor deposition, sputter deposition plating, thermal spraying, or any combination thereof. An imaging and coating process may be used to coat materials used for a portable surgical system (e.g., frame and a whole portable enclosure). Molding may comprise hot isostatic pressing, metal injection molding, injection molding, transfer molding, blow molding, dip molding, rotational molding, shrink wrapping, or any combination thereof. Injection molding may comprise a high pressure injection of raw materials into one or more molds. One or more molds may shape a raw material into a desired shape of components of a portable surgical system. Blow molding may comprise multiple steps. Multiple steps may comprise melting down a raw material, forming a raw material into a parison, placing a parison into a mold, and air blowing through a parison to push a material out to match a mold. Molding may be used to form different components of the portable surgical system (e.g., frame and the one-way sensitive valve). Forming may comprise forging, rolling, extrusion, pressing, bending, shearing, or any combination thereof. Machining may comprise mills, milling, drilling, shaping, industrial finishing, or any combination thereof. Joining may comprise welding, brazing, soldering, sintering, adhesive boding, or any combination thereof. Joining may be used to assemble different components of a portable surgical system (e.g., assembling ports to a portable enclosure). Additive manufacturing processes may be used to create components of a portable surgical system by laying down successive layers of material, each of which can be seen as a thinly sliced horizontal cross-section of a target component.

A portable enclosure may be manufactured as a single (or unitary) piece, thus no assembly may be required. A portable enclosure may be manufactured as two pieces, thus at least one assembly step may be required. Two pieces may be manufactured separately. Two pieces may be manufactured simultaneously. A portable enclosure may be manufactured as three pieces, thus multiple assembly steps may be required. A portable enclosure may include at least two, three, four or more steps. A portable enclosure may be manufactured as more than three pieces.

Computer Control Systems

Figure 7:
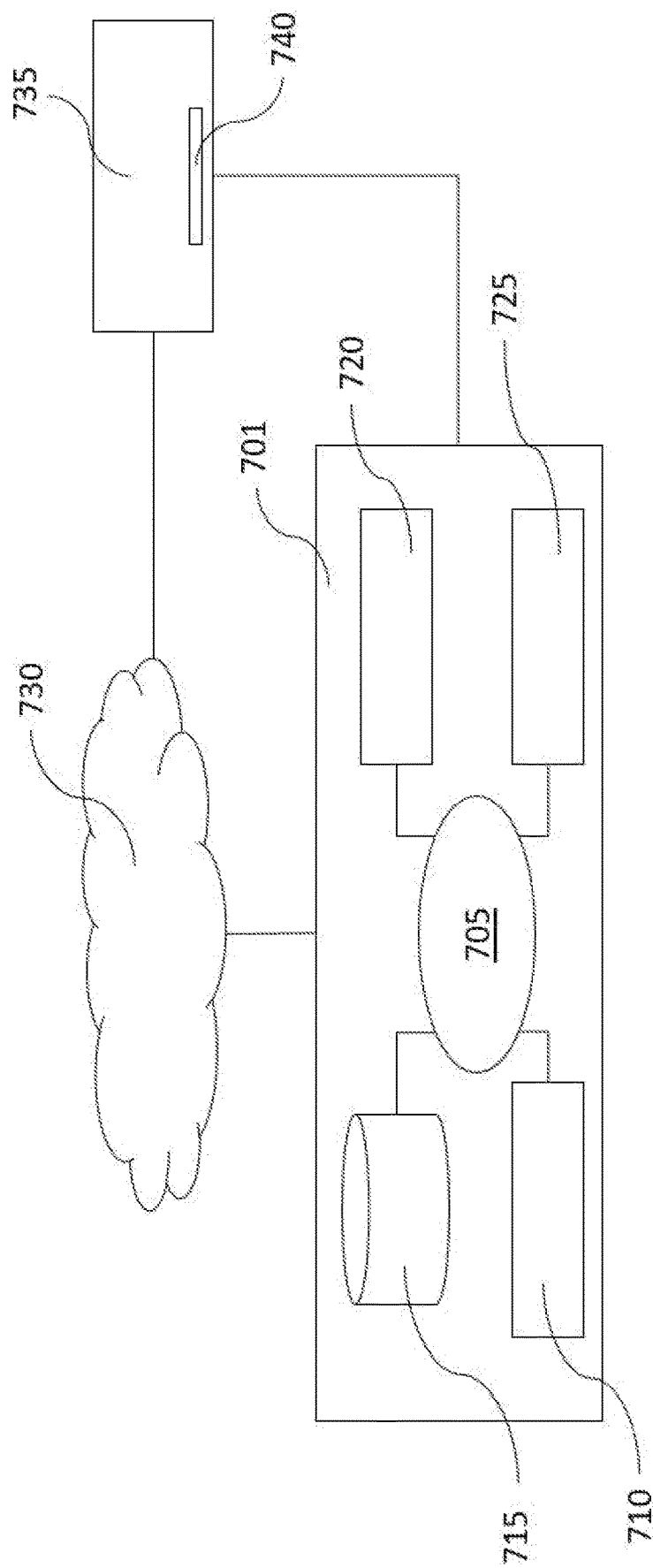
FIG. 7 shows a computer control system that is programmed or otherwise configured to implement methods provided herein.

The present disclosure provides computer control systems that are programmed to implement methods of the disclosure. FIG. 7 shows a computer system 701 that is programmed or otherwise configured to be coupled with a portable enclosure. The computer system 701 can regulate various aspects of a portable surgical system of the present disclosure, such as, for example, receiving data collected from one or more sensors, analyzing data collected from one or more sensors, generating datasets based on the collected data, and generating a control algorithm based on the datasets. The computer system 701 can be an electronic device of a user or a computer system that is remotely located with respect to the electronic device. The electronic device can be a mobile electronic device.

The computer system 701 includes a central processing unit (CPU, also "processor" and "computer processor" herein) 705, which can be a single core or multi core processor, or a plurality of processors for parallel processing. The computer system 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720 and peripheral devices 725 are in communication with the CPU 705 through a communication bus (solid lines), such as a motherboard. The storage unit 715 can be a data storage unit (or data repository) for storing data. The computer system 701 can be operatively coupled to a computer network ("network") 730 with the aid of the communication interface 720. The network 730 can be the Internet, an internet and/or extranet, or an intranet and/or extranet that is in communication with the Internet. The network 730 in some cases is a telecommunication and/or data network. The network 730 can include one or more computer servers, which can enable distributed computing, such as cloud computing. The network 730, in some cases with the aid of the computer system 701, can implement a peer-to-peer network, which may enable devices coupled to the computer system 701 to behave as a client or a server.

The CPU 705 can execute a sequence of machine-readable instructions, which can be embodied in a program or software. The instructions may be stored in a memory location, such as the memory 710. The instructions can be directed to the CPU 705, which can subsequently program or otherwise configure the CPU 705 to implement methods of the present disclosure. Examples of operations performed by the CPU 705 can include fetch, decode, execute, and writeback.

The CPU 705 can be part of a circuit, such as an integrated circuit. One or more other components of the system 701 can be included in the circuit. In some cases, the circuit is an application specific integrated circuit (ASIC).

The storage unit 715 can store files, such as drivers, libraries and saved programs. The storage unit 715 can store user data, e.g., user preferences and user programs. The computer system 701 in some cases can include one or more additional data storage units that are external to the computer system 701, such as located on a remote server that is in communication with the computer system 701 through an intranet or the Internet.

The computer system 701 can communicate with one or more remote computer systems through the network 730. For instance, the computer system 701 can communicate with a remote computer system of a user (e.g., user's cell phone). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 701 via the network 730.

Methods as described herein can be implemented by way of machine (e.g., computer processor) executable code stored on an electronic storage location of the computer system 701, such as, for example, on the memory 710 or electronic storage unit 715. The machine executable or machine readable code can be provided in the form of software. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710.

The code can be pre-compiled and configured for use with a machine having a processor adapted to execute the code or can be compiled during runtime. The code can be supplied in a programming language that can be selected to enable the code to execute in a pre-compiled or as-compiled fashion.

Aspects of the systems and methods provided herein, such as the computer system 701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 701 can include or be in communication with an electronic display 735 that comprises a user interface (UI) 740 for providing, for example, the instruction related to a surgical procedure, the environmental conditions related to a surgical procedure, and a patient's customized surgical procedure. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 705. The algorithm can, for example, train surgical robots to perform different types of surgeries.

EXAMPLES

These examples are provided for illustrative purposes only and not to limit the scope of the claims provided herein.

Example 1—Performing a Surgery with a Portable Surgical System in a Non-Surgical Environment In this example, a surgery is performed by a provider and his/her assistant to a patient in a non-surgical environment. The provider carries a portable surgical system in his/her backpack. The patient's chest is injured in an outdoor space. Upon notice of the injury, the provider lays the patient on a flat surface. Then the provider performs some preoperative procedures, including a skin disinfecting procedure. At the same time, the assistant unfolds a portable enclosure of the portable surgical system, sets up an environmental control system, and places necessary wires or cords inside the portable enclosure through wire ports. After the preoperative procedures, the provider places the portable enclosure on top of the patient and places a drape on the patient's chest to secure the portable enclosure on the patient. The assistant then immediately turns on power for an environmental control system, so clean airflow is pushed into the portable enclosure. The provider places an instrument tray into the portable enclosure through a port. The assistant then adjusts light sources and secures the frames (if there is any) to support the portable enclosure. The provider then starts to perform a surgery on the patient's chest. During the surgery, the assistant manages the environmental control system and one-way pressure sensitive valves to ensure right amount of pressure in the portable enclosure.

Example 2—Collecting Surgical Procedure Data with a Portable Surgical System

In this example, surgical procedure data is collected by one or more sensors of a portable surgical system. The portable surgical system has already been set up, and a provider is about to perform a surgery. Motion sensors are placed on arms and hands of the provider, infrared sensors are placed inside and/or outside of a portable enclosure, and other types of sensors (e.g., humidity sensors) are placed inside and/or outside of the portable enclosure. During the surgery, the motion sensors continuously detect movements of the provider's arms and hands, collect movement data, and send data to a server or a processor for processing. The infrared sensors continuously detect positions of surgical instruments (e.g., scalpel), collect position data, and send data to a server or a processor for processing. The other types of sensors continuously detect environmental parameters (e.g., humidity and temperature) inside and/or outside the portable enclosure, collect environmental data, and send data to a server or a processor for processing.

While exemplary embodiments have been shown and described herein, it will be obvious to those skilled in the art that such embodiments are provided by way of example only. Numerous variations, changes, and substitutions will occur to those skilled in the art. It should be understood that various alternatives to the embodiments described herein may be employed. It is intended that the following claims define the scope of the disclosure and that methods and structures within the scope of these claims and their equivalents be covered thereby.

What is claimed is:

1. A portable surgical system designed for interoperability with surgical or research tools and processes, the portable surgical system comprising:
a portable enclosure separating a surgical environment inside the portable enclosure from a user environment outside the portable enclosure, the portable enclosure comprising a flow tube attached to inside of the portable enclosure and connected to an environmental control system, wherein the flow tube comprises a variable density perforation structure and is configured to provide an essentially uniform laminar airflow inside at least part of the portable enclosure, wherein the variable density perforation structure of the flow tube comprises a first portion of the flow tube with a first density of perforation and a second portion of the flow tube with a second density of perforation, the first density of perforation being greater than the second density of perforation, and the essentially uniform laminar airflow comprising an airflow in the first portion that matches to an airflow in the second portion, and one or more sensors that comprise at least one sensor configured to detect situational or environmental parameters comprising patient vitals and diagnostics, humidity, temperature, pressure, brightness, and other parameters pertinent to efficacy of the portable surgical system.

2. The portable surgical system of claim 1, wherein:
(i) the one or more sensors further comprises at least one motion sensor configured to detect a movement of a surgical instrument, a medical professional, a patient, a surgical robot, or any combination thereof, or
(ii) the portable enclosure further comprises one or more ports allowing for entry, exit, and insertion of surgical and research tools between the surgical environment and the user environment; or
(iii) a combination of both.

3. The portable surgical system of claim 1, further comprising an information processing system configured to process data collected from the one or more sensors.

4. The portable surgical system of claim 3, wherein the information processing system is configured to provide instructions to a surgery robot, provide instructions or alerts to users of the portable enclosure, provide instructions for devices that are designed to be used with the portable enclosure or standard surgical procedures, collect data for use in robotic control, collect data for use in research, collect data for use in quality control and improvement, or any combination thereof.

5. The portable surgical system of claim 4, wherein the instructions comprise information related to a surgical procedure.

6. The portable surgical system of claim 5, further comprising (i) a physical transfer unit configured to transfer information between operators; or (ii) a wireless transfer unit configured to transfer information via frequencies of ELF, SLF, ULF, VLF, LF, MF, HF, VHF, UHF, SHF, EHF, THF, any frequency bands of radio communication for commercial use, light, ultrasounds, or any combination thereof, or (iii) a combination of both.

7. The portable surgical system of claim 5, further comprising a physical information unit separate from a processor, wherein the physical information unit is programmed by the processor through direct or wireless connection.

8. The portable surgical system of claim 7, wherein the physical information unit is configured to pair with a patient during transfer to a different healthcare provider through a wristband, dog tag, programmable implant, or other relevant physical medium.

9. The portable surgical system of claim 3, wherein the portable surgical system is configured to receive the data collected from the one or more sensors, generate procedure information based on the data collected from the one or more sensors, and train a control algorithm using datasets, wherein the datasets are generated using the procedure information.

10. The portable surgical system of claim 9, wherein the data comprises structured data, time-series data, unstructured data, relational data, or any combination thereof, and wherein the unstructured data comprises audio data, image data, video, mechanical data, electrical data, chemical data, and any combination thereof, for use in accurately simulating or training robotics or simulations.

11. The portable surgical system of claim 9, wherein the portable surgical system is configured to conduct (i) analysis of the surgical environment through infrared, visible light, Terahertz, ultraviolet, gamma rays, millimeter waves, microwaves, x-ray, or any combination thereof, or (ii) audio analysis of the surgical environment through microphones, visual vibration analysis, or both; or (iii) mechanical, electrical, and chemical analysis of the surgical environment using the one or more sensors; or (iv) any combination thereof.

12. The portable surgical system of claim 9, wherein the portable surgical system is configured to (i) reconstruct 3 dimensional images based on information detected or recorded; and (ii) fuse additional data with the 3 dimensional images and construct hybrid 3 dimensional images.

13. The portable surgical system of claim 9, wherein the data or datasets produce automatic diagnostic, surgery support, or treatment suggestions based on knowledge bases, expert systems, or other suitable information tools.

14. The portable surgical system of claim 1, wherein the one or more sensors further comprise at least one environmental sensor to detect one or more surgical environment parameters comprising: temperature, pressure, humidity, luminance, heart rate, breathing rate, blood pressure, blood oxygen saturation, electrocardiogramyography, skin conductance, airflow, air quality, internal and external gas composition, a chemical composition of the surgical environment, particulate count and composition, $CO_2$ concentration, or any combination thereof.

15. The portable surgical system of claim 1, wherein the one or more sensors further comprises at least one motion sensor comprising an infrared sensor, optical sensor, microwave sensor, ultrasonic sensor, radio-frequency sensors, magnetic sensor, vibration sensor, acceleration sensor, gyroscopic sensor, tilt sensor, piezoelectric sensor, pressure sensor, strain sensor, flex sensor, electromyographic sensor, electrocardiograma sensor, electroencephalographic sensor, thermal sensor, capacitive touch sensor, resistive touch sensor, proximity sensor, infrared camera, Terahertz camera, position sensor, visible light sensor, visible light camera, or any combination thereof.

16. The portable surgical system of claim 1, wherein (i) a sensor of the one or more sensors, or (ii) an electronics layer, or (iii) both is/are embedded in a wall of the portable enclosure.

17. The portable surgical system of claim 16, wherein the electronics layer comprises the sensor of the one or more sensors and a display screen configured to display parameters, pictures or videos recorded by the one or more sensors, data derived from the parameters, pictures or videos recorded by a camera of the one or more sensors, or a combination thereof.

18. The portable surgical system of claim 1, wherein the one or more sensors further comprise a video camera for 3 dimensional vision, and wherein the video camera for 3 dimensional vision is a time of flight camera.

19. The portable surgical system of claim 1, further comprising:
(c) a human operator interface comprising at least a display and a command console, wherein the display is configured to display information according to commands received from the command console, wherein the display is inside the portable enclosure, outside the portable enclosure, or embedded in a wall of the portable enclosure, wherein the command console is inside the portable enclosure, outside the portable enclosure, or embedded in a wall of the portable enclosure.

20. The portable surgical system of claim 1, wherein data or datasets are uploaded to a cloud-based database.

* * * * *

UNITED STATES PATENT AND TRADEMARK OFFICE
CERTIFICATE OF CORRECTION

PATENT NO. : 12,324,711 B2  
APPLICATION NO. : 17/276622  
DATED : June 10, 2025  
INVENTOR(S) : Stephen Michael Okajima et al.

Page 1 of 1

It is certified that error appears in the above-identified patent and that said Letters Patent is hereby corrected as shown below:

In the Claims

Column 44, Line 39, Claim 6, delete "thereof," and insert -- thereof; --.

Column 44, Line 67, Claim 11, delete "thereof," and insert -- thereof; --.

Column 45, Line 7-8, Claim 12, delete "3 dimensional" and insert -- 3-dimensional --.

Column 45, Line 9, Claim 12, delete "3 dimensional" and insert -- 3-dimensional --.

Column 45, Line 10, Claim 12, delete "3 dimensional" and insert -- 3-dimensional --.

Column 45, Line 20, Claim 14, delete "electrocardiogramyography" and insert -- electrocardiography, electromyography, --.

Column 45, Line 33, Claim 15, delete "electrocardiograma" and insert -- electrocardiographic --.

Column 46, Line 16-17, Claim 18, delete "3 dimensional" and insert -- 3-dimensional --.

Column 46, Line 17-18, Claim 18, delete "3 dimensional" and insert -- 3-dimensional --.

Column 46, Line 21, Claim 19, before "a human" delete "(c)".

Signed and Sealed this  
Second Day of September, 2025

Coke Morgan Stewart  
*Acting Director of the United States Patent and Trademark Office*